US008202869B2

(12) United States Patent
Kase et al.

(10) Patent No.: US 8,202,869 B2
(45) Date of Patent: Jun. 19, 2012

(54) METHOD OF TREATING AN ANXIETY DISORDER

(75) Inventors: Hiroshi Kase, Koganei (JP); Naoki Seno, Moriya (JP); Shizuo Shiozaki, Fuji (JP); Minoru Kobayashi, Sunto-gun (JP); Junya Kase, Sunto-gun (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 197 days.

(21) Appl. No.: 10/553,250

(22) PCT Filed: Jun. 10, 2004

(86) PCT No.: PCT/JP2004/008486
§ 371 (c)(1),
(2), (4) Date: Oct. 17, 2005

(87) PCT Pub. No.: WO2004/108137
PCT Pub. Date: Dec. 16, 2004

(65) Prior Publication Data
US 2006/0281770 A1 Dec. 14, 2006

Related U.S. Application Data

(60) Provisional application No. 60/532,793, filed on Dec. 24, 2003, provisional application No. 60/509,046, filed on Jun. 10, 2003.

(51) Int. Cl.
*A61K 31/50* (2006.01)
*A61K 31/41* (2006.01)

(52) U.S. Cl. .................................. 514/252.06; 514/383
(58) Field of Classification Search ............ 514/252.06, 514/383
See application file for complete search history.

(56) References Cited

U.S. PATENT DOCUMENTS

| | | | |
|---|---|---|---|
| 5,047,534 A | * | 9/1991 | Peet et al. ..................... 544/267 |
| 5,543,415 A | | 8/1996 | Suzuki et al. |
| 6,545,000 B1 | | 4/2003 | Shimada et al. |
| 2003/0139395 A1 | * | 7/2003 | Greenlee et al. ............. 514/220 |
| 2006/0128694 A1 | * | 6/2006 | Grzelak et al. ................ 514/220 |

FOREIGN PATENT DOCUMENTS
EP  1 177 797  *  6/2002

OTHER PUBLICATIONS

Hirani et al. Evaluation of [4-O-methyl-11C]KW-6002 as a potential PET ligand for mapping central adenosine A2A receptors in rats. Synapse 42: 164-176, 2001.*
Goodman & Gilman's: The Pharmacological Basis of Therapeutics, Tenth Edition, 2001, p. 469.*

* cited by examiner

*Primary Examiner* — Renee Claytor
(74) *Attorney, Agent, or Firm* — Fitzpatrick, Cella, Harper & Scinto

(57) ABSTRACT

Anxiety disorders, such as panic disorder, agoraphobia, obsessive-compulsive disorder, social phobia, post-traumatic stress disorder, generalized anxiety disorder, specific phobia, or the like, are treated by administering an effective amount of at least one adenosine $A_{2A}$ receptor antagonist to a patient in need thereof, optionally in combination with an anxiolytic(s) other than the adenosine $A_{2A}$ receptor antagonist.

6 Claims, 1 Drawing Sheet

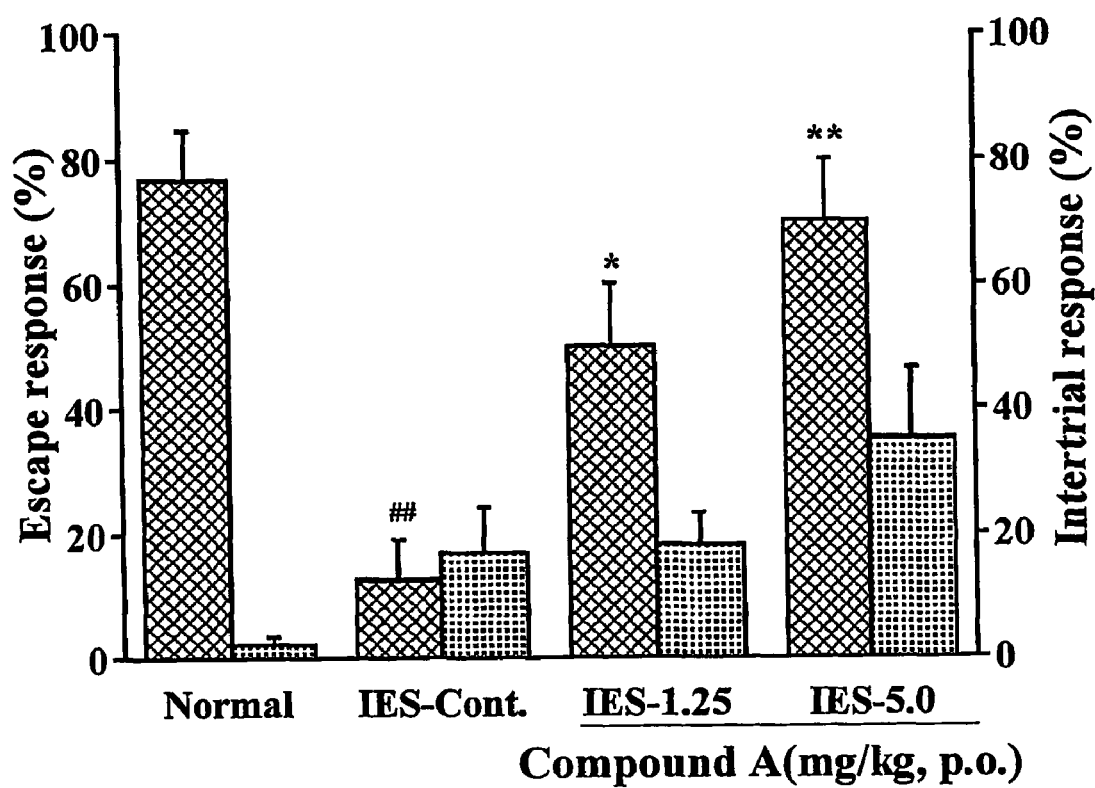

METHOD OF TREATING AN ANXIETY DISORDER

FIELD OF THE INVENTION

The present invention relates to methods of treating an anxiety disorder comprising administering at least one adenosine $A_{2A}$ receptor antagonist.

BACKGROUND OF THE INVENTION

Anxiety Disorders

Anxiety disorders are a group of psychological problems whose key features include excessive anxiety, fear, worry, avoidance, and compulsive rituals, and produce or result in inordinate morbidity, overutilization of healthcare services, and functional impairment. They are among the most prevalent psychiatric condition in the United States and in most other countries. An incidence of the illness is fairly uniform across cultures. In most cases women are more likely than men to experience anxiety disorders. Chronic anxiety disorders may increase the rate of cardiovascular-related mortality, and hence the proper diagnosis and rapid initiation of treatment must be made.

Anxiety disorders listed in the Diagnostic and Statistical Manual of Mental Disorders (Fourth Edition Revised, 1994, published by the American Psychiatric Association, Washington, D.C., U.S.A., pages 393 to 444), include panic disorder with and without agoraphobia, agoraphobia without history of panic disorder, specific phobia, social phobia, obsessive-compulsive disorder (OCD), post-traumatic stress disorder (PTSD), acute stress disorder, generalized anxiety disorder (GAD), anxiety disorder due to a general medical condition, substance-induced anxiety disorder, specific phobia, and anxiety disorder not otherwise specified.

Panic Disorder With and Without Agoraphobia

Panic disorder is an anxiety disorder whose essential feature is the presence of recurrent panic attacks (i.e. discrete periods of intense fear or discomfort with at least four characteristic associated symptoms). The attacks usually last minutes (or, rarely, hours), are unexpected and do not, as in simple phobia, tend to occur immediately before or on exposure to a situation that almost always causes anxiety. The "unexpected" aspect of the attacks is an essential feature of the disorder. Panic attacks typically begin with the sudden onset of intense apprehension or fear, and are accompanied by physical symptoms such as shortness of breath, dizziness, faintness, choking, palpitations, trembling, sweating, shaking, nausea, numbness, hot flushes or chills, chest pain or the like. Panic disorder may be associated with agoraphobia, in severe cases of which the person concerned is virtually housebound.

Approximately one-third to one-half of individuals diagnosed with panic disorder in community samples also have agoraphobia, although a much higher rate of agoraphobia is encountered in clinical samples.

Agoraphobia Without History of Panic Disorder

Agoraphobia is a condition characterized by the feature of anxiety about being in places or situations from which escape might be difficult (or embarrassing) or in which help may not be available in the event of having a panic attack or panic-like symptoms (e.g., fear of having a sudden attack of dizziness or a sudden attack of diarrhea). Agoraphobia occurs in the context of panic disorder with agoraphobia and agoraphobia without history of panic disorder. The essential features of agoraphobia without history of panic disorder are similar to those of panic disorder with agoraphobia except the focus of fear is on the occurrence of incapacitating or extremely embarrassing panic-like symptoms or limited symptom attacks rather than full panic attacks.

Almost all individuals (over 95%) who present with agoraphobia also have a current diagnosis (or history) or panic disorder. In contrast, the prevalence of agoraphobia without history of panic disorder in epidemiological samples has been reported to be higher than that for panic disorder with agoraphobia.

Obsessive-Compulsive Disorder (OCD)

The primary symptom is recurrent obsessions (i.e., recurrent and intrusive thoughts, images or urges that cause marked anxiety) and/or compulsions (i.e., repetitive behaviors or mental acts that are performed to reduce the anxiety generated by one's obsessions) of sufficient severity to cause distress, be time consuming or to interfere significantly with a person's normal routine or lifestyle. Anxiety is an associated feature of this disorder: an affected person may, for example, show a phobic avoidance of situations that involve the cause of the obsession. Typical obsessions concern contamination, doubting (including self-doubt) and disturbing sexual or religious thoughts. Typical compulsions include washing, checking, ordering things, and counting.

Social Phobia

Social phobia is characterized by the persistent fear of social or performance situations in which embarrassment may occur. Typical situations feared or avoided by individuals with social phoebe include parties, meetings, eating in front of others, writing in front of others, public speaking, conversations, meeting new people, and other related situations. Exposure to social or performance situations almost invariably provokes an immediate anxiety response, as well as sweating, trembling, racing or pounding heart beat, mental confusion, and a desire to flee. Social avoidance and isolation can also become extreme, especially in the more generalized condition. Alcohol abuse is more commonly associated with social phobia than any other anxiety disorder, and frequently represents an attempt at self medication of social fears.

Post-Traumatic Stress Disorder (PTSD)

The principal characteristic symptoms involve re-experiencing a traumatic (i.e. psychologically distressing) event, the avoidance of stimuli associated with that event, the numbing of general responsiveness, and increased arousal. The "events" concerned are outside the range of common experiences such as simple bereavement, chronic illness and marital conflict.

Generalized Anxiety Disorder (GAD)

GAD is a condition of which the essential feature is unrealistic or excessive anxiety, and worry about two or more life circumstances for six months or longer. The worry must be experienced as difficult to control and during that time the affected person is bothered by the concerns for more days than not. When the person is anxious he or she manifests signs of motor tension, autonomic hyperactivity and vigilance and scanning.

Specific Phobia

Specific phobia is an anxiety disorder of which the essential feature is a persistent fear of a circumscribed stimulus, which may be an object or situation, other than fear of having a panic attack or of humiliation or embarrassment in social situations (which falls under social phobia). Examples include phobias of flying, heights, animals, injections, and blood. Simple phobias may be referred to as "specific" phobias and, in the population at large. Exposure to the phobic stimulus will almost invariably lead to an immediate anxiety response.

Multiple causes are suspected for anxiety disorders, especially a combination of genetic makeup, early growth and development, and later life experience. The anxiety disorders are treated with some form of counseling or psychotherapy or pharmacotherapy (drug therapy), either singly or in combination. The medications typically used to treat patients with anxiety disorders are benzodiazepines, selective serotonin reuptake inhibitors (SSRIs), and buspirone.

The benzodiazepines are a large class of relatively safe and widely prescribed medications that have rapid and profound antianxiety and sedative-hypnotic effects. Drugs within the SSRI class are used for the treatment of anxiety disorders such as panic disorder, agoraphobia, OCD, social phobia, post-traumatic stress disorder, specific phobia and broader anxiety disorders [Kaplan & Sadock's Comprehensive textbook of psychiatry 7th. edition, 1, 1441-1498 (1999)]. Buspirone is a relatively selective $5HT_{1A}$ partial agonist, approved by the FDA as an anxiolytic, most useful for the treatment of GAD, and now frequently used as an adjunct to SSRIs [Kaplan & Sadock's Comprehensive textbook of psychiatry 7th. edition, 1, 1441-1498 (1999)].

There appears to be effective pharmacological and psychological treatments for GAD. Although almost medication studies are based on old criteria for GAD (which have since been substantially revised), there is evidence that a range of pharmacological interventions may be helpful for GAD, including buspirone, imipramine and a variety of benzodiazepines. Pharmacotherapy is considered less effective in GAD than in some other anxiety disorders (Kaplan & Sadock's Comprehensive textbook of psychiatry 7th. edition, 1, 1441-1498 (1999)]. Treatment is usually behavioral exposure. Medications are used occasionally to alleviate the anticipatory anxiety associated with beginning exposure treatment. Low-dose benzodiazepines and β-adrenergic receptor antagonists can be used for this purpose on an as-needed basis.

Concerns have been expressed over possible side effect of some of the medications used to treat anxiety disorders, particularly the benzodiazepines. Common side effects associated with these medications, which may decrease over the course of treatment, include sedation, fatigue, ataxia, slurred speech, and amnesia. Benzodiadepines have also the potential for producing drug dependence (i.e. physiological or behavioral symptoms after discontinuation of use).

There is therefore a continuing need for new agents that are effective and safety anxiolytics.

Adenosine $A_{2A}$ Receptors

Adenosine is known to act via four major receptor subtypes, $A_1$, $A_{2A}$, $A_{2B}$, and $A_3$, which have been characterized according to their primary sequences [Pharmacol. Rev., 46, 143-156 (1994)]. Adenosine $A_{2A}$ receptors are abundant in the basal ganglia, especially in the caudate-putamen, nucleus accumbens, and olfactory tubercle in several species [Brain Res., 519, 333-337 (1990)]. The basal ganglia are a critical component of subcortical circuits involved in the integration of sensorimotor, associative, and limbic information to produce motor behavior. In the caudate-putamen, one of the major nuclei in the basal ganglia, adenosine $A_{2A}$ receptors are localized on several neurons and have been shown to modulate the neurotransmission of α-aminobutyric acid (GABA), acetylcholine and glutamate [J. Neurochem., 66, 1882-1888 (1996); J. Neurosci., 16, 605-611 (1996); J. Physiol., 532, 423-434 (2001); Neuroscience, 100; 53-62 (2000); Trends Pharmacol. Sci., 18, 338-344 (1997); and Biosci. Biotechnol. Biochem., 65, 1447-1457 (2001)]. Indeed, adenosine $A_{2A}$ receptor antagonists exhibit significant antiparkinsonian activity [Ann. Neurol., 43, 507-513 (1998); Neurology, 52, 1673-1677 (1999); and Biosci. Biotechnol. Biochem., 65, 1447-1457 (2001)]. Furthermore, current studies suggest linking reward expectation, attention, and cognitions to behavior in the basal ganglia.

More recently, the neuroprotective effect of an adenosine $A_{2A}$ receptor antagonist has been demonstrated in MPTP-induced dopaminergic neurodegeneration [J. Neurochem., 80, 262-270 (2002); and J. Neurosci., 21, RC143 (1-6) (2001)].

Some xanthine compounds are known to show adenosine $A_{2A}$ receptor antagonistic activity, anti-Parkinson's disease activity, antidepressant activity, inhibitory activity on neurodegeneration, or the like (U.S. Pat. Nos. 5,484,920; 5,587,378; and 5,543,415; EP 1016407A1; etc.)

(E)-3-(3-Hydroxypropyl)-1-propyl-8-styrylxanthine is reported to have an anxiolytic activity [Society for Neuroscience Abstracts, (2000). Vol. 26, No. 1-2, pp. Abstract No.-868.17. print. Meeting Info.: 30th Annual Meeting of the Society of Neuroscience New Orleans, La., USA Nov. 4-09, 2000].

Some triazolopyrimidines are reported to have an affinity toward the $A_{2A}$ receptor (WO 02/48145 etc.)

A combination of an adenosine $A_{2A}$ receptor antagonist and an antidepressant or anxiolytic is reported (WO 03/022283). However, there is no data showing the effect of the combination of an adenosine $A_{2A}$ receptor antagonist and an anxiolytic in the above publication.

SUMMARY OF THE INVENTION

The object of the present invention is to provide a method of treating an anxiety disorder, such as panic disorder, agoraphobia, obsessive-compulsive disorder, social phobia, post-traumatic stress disorder, generalized anxiety disorder, specific phobia, or the like.

DETAILED DESCRIPTION OF THE INVENTION

The present invention relates to the following (1) to (88).

(1) A method of treating an anxiety disorder selected from the group consisting of panic disorder, agoraphobia, obsessive-compulsive disorder, social phobia, post-traumatic stress disorder, and specific phobia, comprising administering an effective amount of at least one adenosine $A_{2A}$ receptor antagonist to a patient in need thereof.

(2) The method of treating an anxiety disorder according to the above (1) wherein the adenosine $A_{2A}$ receptor antagonist is a xanthine derivative or a pharmaceutically acceptable salt thereof.

(3) The method of treating an anxiety disorder according to the above (1) wherein the adenosine $A_{2A}$ receptor antagonist is a compound represented by formula (I):

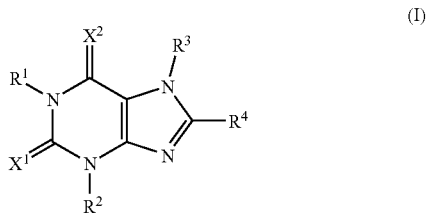

(I)

[wherein $R^1$, $R^2$ and $R^3$ independently represent hydrogen, lower alkyl, lower alkenyl or lower alkynyl; $R^4$ represents cycloalkyl, $-(CH_2)_n-R^5$ (in which $R^5$ represents substituted or unsubstituted aryl, or a substituted or unsubstituted heterocyclic group; and n is an integer of 0 to 4) or formula (I-i)

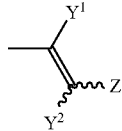

(I-i)

(in which $Y^1$ and $Y^2$ independently represent hydrogen, halogen or lower alkyl; and Z represents substituted or unsubstituted aryl, or a substituted or unsubstituted heterocyclic group); and $X^1$ and $X^2$ independently represent O or S], or a pharmaceutically acceptable salt thereof.

(4) The method of treating an anxiety disorder according to the above (1) wherein the $A_{2A}$ receptor antagonist is a compound represented by formula (I-A):

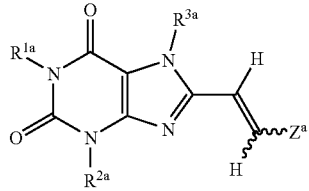

(I-A)

[wherein $R^{1a}$ and $R^{2a}$ independently represent methyl or ethyl; $R^{3a}$ represents hydrogen or lower alkyl; and $Z^a$ represents formula (I-ii)

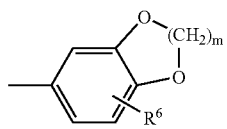

(I-ii)

(in which $R^6$ represents hydrogen, hydroxy, lower alkyl, sower alkoxy, halogen, nitro or amino; and m represents an integer of 1 to 3) or formula (I-iii)

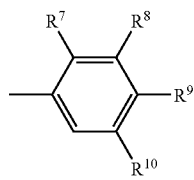

(I-iii)

(in which at least one of $R^7$, $R^8$ and $R^9$ represents lower alkyl or lower alkoxy and the others represent hydrogen; $R^{10}$ represents hydrogen or lower alkyl)], or a pharmaceutically acceptable salt thereof.

(5) The method of treating an anxiety disorder according to the above (1) wherein the adenosine $A_{2A}$ receptor antagonist is a compound represented by formula (I-B):

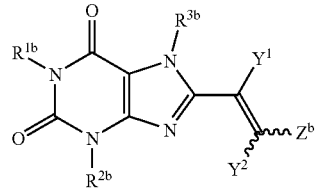

(I-B)

[wherein $R^{1b}$ and $R^{2b}$ independently represent hydrogen, propyl, butyl, lower alkenyl or lower alkynyl; $R^{3b}$ represents hydrogen or lower alkyl; $Z^b$ represents substituted or unsubstituted naphthyl, or formula (I-ii)

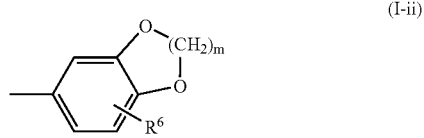

(I-ii)

(in which $R^6$ and m have the same meanings as defined above, respectively); and $Y^1$ and $Y^2$ have the same meanings as defined above, respectively], or a pharmaceutically acceptable salt thereof.

(6) The method of treating an anxiety disorder according to the above (1) wherein the adenosine $A_{2A}$ receptor antagonist is (E)-8-(3,4-dimethoxystyryl)-1,3-diethyl-7-methylxanthine or a pharmaceutically acceptable salt thereof.

(7) The method of treating an anxiety disorder according to the above (1) wherein the adenosine $A_{2A}$ receptor antagonist is a compound represented by formula (II):

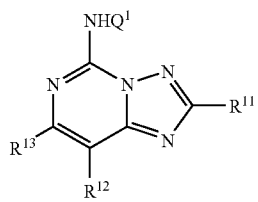

(II)

[wherein $R^{11}$ represents substituted or unsubstituted aryl, or a substituted or unsubstituted heterocyclic group; $R^{12}$ represents hydrogen, halogen, substituted or unsubstituted lower alkyl, substituted or unsubstituted aryl, or a substituted or unsubstituted heterocyclic group; $R^{13}$ represents hydrogen, halogen or —$WR^{14}$ (in which W represents —O— or —S—; and $R^{14}$ represents substituted or unsubstituted lower alkyl, substituted or unsubstituted aryl, or a substituted or unsubstituted heterocyclic group); and $Q^1$ represents hydrogen or 3,4-dimethoxybenzyl} {e.g. 5-amino-7-(4-benzoylpiperazinyl)-2-(2-furyl)[1,2,4]triazolo[1,5-c]pyrimidine}, or a pharmaceutically acceptable salt thereof.

(8) The method of treating an anxiety disorder according to the above (1) wherein the adenosine $A_{2A}$ receptor antagonist is a compound represented by formula (III):

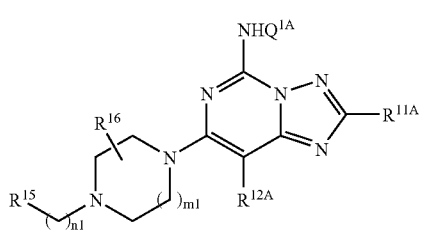

(III)

[wherein $R^{11A}$ represents substituted or unsubstituted aryl, or substituted or unsubstituted heteroaryl; $R^{12A}$ represents hydrogen, halogen, substituted or unsubstituted lower alkyl, substituted or unsubstituted aryl, or substituted or unsubstituted heteroaryl; m1 and n1 are independently an integer of 0 to 4; $Q^{1A}$ represents hydrogen or 3,4-dimethoxybenzyl; $R^{15}$ represents hydrogen, substituted or unsubstituted aryl, a substituted or unsubstituted heterocyalic group, or —$CR^{17}R^{18}R^{19}$ (in which $R^{17}$, $R^{18}$ and $R^{19}$ independently represent hydrogen, hydroxy, substituted or unsubstituted lower alkyl, substituted or unsubstituted lower alkoxy, substituted or unsubstituted aryl, or a substituted or unsubstituted heterocyalic group; or $R^{18}$ and $R^{19}$ are combined together with an adjacent carbon atom to form a substituted or unsubstituted carbon ring); and $R^{16}$ represents hydrogen, halogen, hydroxy, or substituted or unsubstituted lower alkyl], or a pharmaceutically acceptable salt thereof.

(9) The method of treating an anxiety disorder according to the above (1) wherein the adenosine $A_{2A}$ receptor antagonist is a compound represented by formula (III-A):

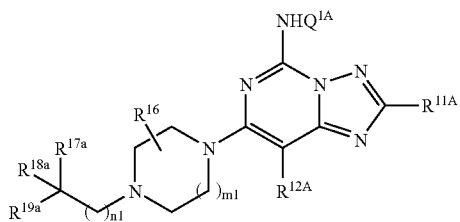

(III-A)

(wherein $Q^{1A}$, $R^{11A}$, $R^{12A}$, $R^{16}$, m1 and n1 have the same meanings as defined above, respectively; $R^{17a}$ represents hydroxy, hydroxyl-substituted lower alkyl, substituted or unsubstituted lower alkoxy, or imidazo[1,2-a]pyridyl; and $R^{18a}$ and $R^{19a}$ independently represent hydrogen, substituted or unsubstituted lower alkyl, or substituted or unsubstituted aryl; or $R^{18a}$ and $R^{19a}$ are combined together with an adjacent carbon atom to form a substituted or unsubstituted carbon ring) {e.g. 5-amino-2-(2-furyl)-7-[4-(2-hydroxy-2-methylpropyl)piperazinyl][1,2,4]triazolo[1,5-c]pyrimidine, and 5-amino-2-(2-furyl)-7-[4-(3-hydroxy-3-methylbutyl)piperazinyl][1,2,4]triazolo[1,5-c]pyrimidine}, or a pharmaceutically acceptable salt thereof.

(10) The method of treating an anxiety disorder according to the above (1) wherein the adenosine $A_{2A}$ receptor antagonist is a compound represented by formula (IV):

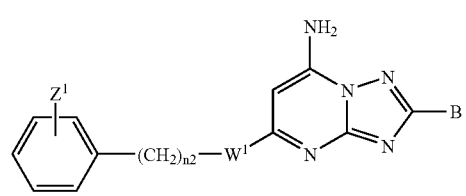

(IV)

(wherein B represents furyl or thienyl; $W^1$ represents a single bond, —O— or —S—; $Z^1$ represents hydrogen, halogen, or substituted or unsubstituted lower alkyl; and n2 is an integer of 0 to 5) {e.g. 7-amino-2-(2-furyl)-5-phenoxy[1,2,4]triazolo[1,5-a]pyrimidine}, or a pharmaceutically acceptable salt thereof.

(11) The method of treating an anxiety disorder according to the above (1) wherein the adenosine $A_{2A}$ receptor antagonist is a compound represented by formula (V):

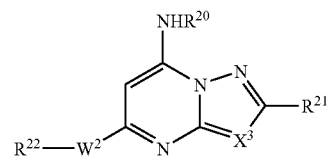

(V)

[wherein $R^{20}$ represents hydrogen, substituted or unsubstituted lower alkyl, or substituted or unsubstituted lower alkanoyl; $R^{21}$ represents a substituted or unsubstituted heterocyclic group; $R^{22}$ represents hydrogen, substituted or unsubstituted lower alkyl, substituted or unsubstituted lower alkenyl, substituted or unsubstituted cycloalkyl, substituted or unsubstituted aryl, or a substituted or unsubstituted heterocyclic group; $W^2$ represents a single bond, —O—, —S—, —S(=O)—, —S(=O)$_2$— or —$NR^{23}$— (in which $R^{23}$ represents hydrogen, or substituted or unsubstituted lower alkyl); and $X^3$ represents N or $CR^{24}$ (in which $R^{24}$ represents hydrogen, or substituted or unsubstituted lower alkyl)], or a pharmaceutically acceptable salt thereof.

(12) The method of treating an anxiety disorder according to the above (1) wherein the adenosine $A_{2A}$ receptor antagonist is a compound represented by formula (VI):

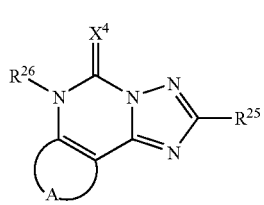

(VI)

[wherein $R^{25}$ represents substituted or unsubstituted aryl, or a substituted or unsubstituted heterocyclic group; $R^{26}$ represents hydrogen, substituted or unsubstituted lower alkyl, substituted or unsubstituted lower alkenyl, substituted or unsubstituted lower alkynyl, substituted or unsubstituted cycloalkyl, substituted or unsubstituted aryl, or a substituted or unsubstituted heterocyclic group; $X^4$ represents O, S or $NR^{27}$ (in which $R^{27}$ represents hydrogen, substituted or unsubstituted lower alkyl, substituted or unsubstituted cycloalkyl, or substituted or unsubstituted aryl); and B and the adjacent two carbon atoms are combined to form a substituted or unsubstituted carbon ring, or a substituted or unsubstituted heterocyclic ring], or a pharmaceutically acceptable salt thereof.

(13) The method of treating an anxiety disorder according to the above (1) wherein the adenosine $A_{2A}$ receptor antagonist is a compound represented by formula (VII):

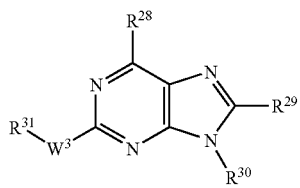

(VII)

[wherein $W^3$ represents —CH$_2$CH$_2$—, —CH=CH— or —CC—; $R^{28}$ represents hydrogen, hydroxy, substituted or unsubstituted lower alkyl, substituted or unsubstituted amino, or a substituted or unsubstituted heterocyclic group; $R^{29}$ represents hydrogen, substituted or unsubstituted cycloalkyl, substituted or unsubstituted aryl, substituted or unsubstituted heteroaryl, or substituted or unsubstituted lower alkenyl; and $R^{30}$ represents hydrogen, substituted or unsubstituted lower alkyl, substituted or unsubstituted cycloalkyl, substituted or unsubstituted aryl, substituted or unsubstituted heteroaryl, substituted or unsubstituted lower alkenyl, or substituted or unsubstituted lower alkynyl; $R^{31}$ represents substituted or unsubstituted lower alkyl, or substituted or unsubstituted aryl] {e.g. 4-[6-amino-8-(3-fluorophenyl)-9-methyl-9H-2-fluorenyl]-2-methyl-3-butyn-2-ol}, or a pharmaceutically acceptable salt thereof.

(14) The method of treating an anxiety disorder according to the above (1) wherein the adenosine $A_{2A}$ receptor antagonist is a compound represented by formula (VIII):

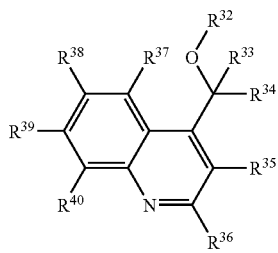

(VIII)

(wherein $R^{32}$ represents hydrogen, or substituted or unsubstituted lower alkyl; $R^{33}$ and $R^{34}$ independently represent hydrogen, substituted or unsubstituted lower alkyl, or substituted or unsubstituted aryl; and $R^{35}$, $R^{36}$, $R^{37}$, $R^{38}$, $R^{39}$ and $R^{40}$ independently represent hydrogen, substituted or unsubstituted lower alkyl, substituted or unsubstituted aryl, or a substituted or unsubstituted heterocyclic group), or a pharmaceutically acceptable salt thereof.

(15) The method of treating an anxiety disorder according to the above (1) wherein the adenosine $A_{2A}$ receptor antagonist is a compound represented by formula (IX):

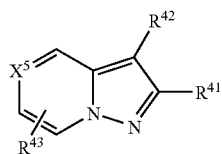

(IX)

(wherein $X^5$ represents CH or N; $R^{41}$ represents lower alkyl, substituted or unsubstituted aryl, or a substituted or unsubstituted heterocyclic group; $R^{42}$ represents substituted or unsubstituted lower alkyl, or a substituted or unsubstituted heterocyclic group; and $R^{43}$ represents hydroxy, halogen, or substituted or unsubstituted lower alkyl) {e.g. 3-[2-(thiazol-2-ylmethyl)-3-oxo-2,3-dihydropyridazin-6-yl]-2-phenylpyrazolo[1,5-a]pyridine}, or a pharmaceutically acceptable salt thereof.

(16) The method of treating an anxiety disorder method according to the above (1) wherein the adenosine $A^{2A}$ receptor antagonist is a compound represented by formula (X):

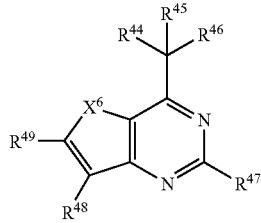

(X)

(wherein $X^6$ represents O or S; $R^{44}$ and $R^{45}$ independently represent hydrogen, hydroxy, cyano, nitro, substituted or unsubstituted lower alkyl, substituted or unsubstituted lower alkoxy, or substituted or unsubstituted aryl; or $R^{44}$ and $R^{45}$ are combined together to form oxo, hydroxyimino, imino or hydrazono; $R^{46}$ represents substituted or unsubstituted lower alkyl or substituted or unsubstituted aryl; and $R^{47}$, $R^{48}$ and $R^{49}$ independently represent hydroxy, halogen, cyano, nitro, substituted or unsubstituted lower alkyl, substituted or unsubstituted lower alkoxy, or substituted or unsubstituted aryl) {e.g. (2R)-2-(1-hydroxy-2-propylamino)thieno[3,2-d]pyrimidin-4-yl 2-thienylmethanone}, or a pharmaceutically acceptable salt thereof.

(17) The method of treating an anxiety disorder according to the above (1) wherein the adenosine $A_{2A}$ receptor antagonist is a compound represented by formula (XI):

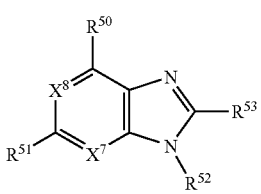

(XI)

(wherein $R^{50}$ represents hydrogen, hydroxy, halogen, substituted or unsubstituted lower alkyl, or substituted or unsubstituted amino; $R^{51}$ represents hydrogen, halogen, substituted or unsubstituted lower alkyl, substituted or unsubstituted lower alkenyl, substituted or unsubstituted lower alkynyl, substituted or unsubstituted lower alkoxy, or substituted or unsubstituted amino; $R^{52}$ represents substituted or unsubstituted lower alkyl, substituted or unsubstituted aryl, or substituted or unsubstituted heteroaryl; $R^{53}$ represents substituted or unsubstituted aryl, or substituted or unsubstituted heteroaryl; and $X^7$ and $X^8$ independently represent N or CH) {e.g. 5-[6-amino-8-(3-fluorophenyl)-9H-9-purinyl]-1-methyl-1,2-dihydro-2-pyrimidine}, or a pharmaceutically acceptable salt thereof.

(18) The method of treating an anxiety disorder according to the above (1) wherein the adenosine $A_{2A}$ receptor antagonist is a compound represented by formula (XII):

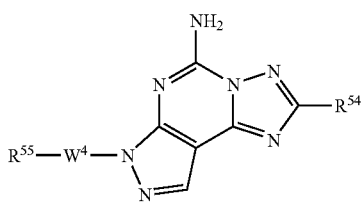

(XII)

(wherein $R^{54}$ represents substituted or unsubstituted aryl, substituted or unsubstituted cycloalkenyl, or substituted or unsubstituted heteroaryl; $W^4$ represents a single bond or —C(=O)—; and $R^{55}$ represents substituted or unsubstituted lower alkyl), or a pharmaceutically acceptable salt thereof.

(19) The method of treating an anxiety disorder according to the above (1) wherein the adenosine $A_{2A}$ receptor antagonist is a compound represented by formula (XIII):

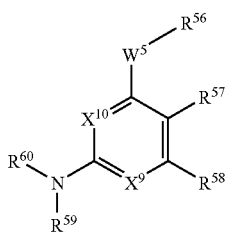

(XIII)

[wherein $W^5$ represents a single bond, —S—, —N($R^{61}$)— (in which $R^{61}$ represents hydrogen, or substituted or unsubstituted lower alkyl), —(CH$_2$)$_2$—, —CH=CH—, —CC— or —O—; $X^9$ and $X^{10}$ independently represents N or CH; $R^{56}$ represents hydrogen, halogen, cyano, substituted or unsubstituted lower alkyl, substituted or unsubstituted lower alkenyl, substituted or unsubstituted lower alkynyl, or substituted or unsubstituted cycloalkyl; $R^{57}$ represents hydrogen, halogen, cyano, nitro, substituted or unsubstituted lower alkyl, substituted or unsubstituted lower alkenyl, or substituted or unsubstituted aryl; $R^{58}$ represents substituted or unsubstituted lower alkyl, substituted or unsubstituted aryl, or substituted or unsubstituted heteroaryl; and $R^{59}$ and $R^{60}$ independently represent hydrogen, or substituted or unsubstituted aryl], or a pharmaceutically acceptable salt thereof.

(20) The method of treating an anxiety disorder according to the above (1) wherein the adenosine $A_{2A}$ receptor antagonist is a compound represented by formula (XIV):

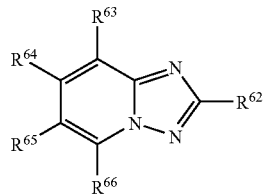

(XIV)

(wherein $R^{62}$ represents substituted or unsubstituted lower alkoxy, substituted or unsubstituted aryl, or substituted or unsubstituted heteroaryl; $R^{63}$ and $R^{65}$ independently represent hydrogen, cyano or phenylsulfonyl; $R^{64}$ represents hydrogen, halogen, substituted or unsubstituted aryl, substituted or unsubstituted heteroaryl, or substituted or unsubstituted amino; and $R^{66}$ represents substituted or unsubstituted amino) {e.g. 2-(4,5-dihydro-furan-2-yl)-7-m-tolyl-[1,2,4] triazolo[1,5-a]pyridin-5-ylamine}, or a pharmaceutically acceptable salt thereof.

(21) The method of treating an anxiety disorder according to the above (1) wherein the adenosine $A_{2A}$ receptor antagonist is a compound represented by formula (XV):

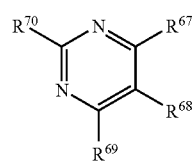

(XV)

(wherein $R^{67}$ represents substituted or unsubstituted aryl, or substituted or unsubstituted heteroaryl; $R^{68}$ represents substituted or unsubstituted heteroaryl; $R^{69}$ and $R^{70}$ independently represent hydrogen, or substituted or unsubstituted amino), or a pharmaceutically acceptable salt thereof.

(22) The method of treating an anxiety disorder according to the above (1) wherein the adenosine $A_{2A}$ receptor antagonist is a compound represented by formula (XVI):

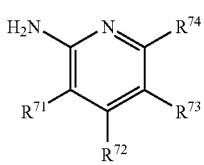

(XVI)

(wherein $R^{71}$ represents cyano, carboxy, or substituted or unsubstituted carbamoyl; $R^{72}$ represents hydrogen, hydroxy, substituted or unsubstituted lower alkoxy, substituted or unsubstituted aryl, or substituted or unsubstituted heteroaryl; and $R^{73}$ and $R^{74}$ independently represent substituted or unsubstituted aryl, or a substituted or unsubstituted heterocyclic group), or a pharmaceutically acceptable salt thereof.

(23) The method of treating an anxiety disorder according to the above (1) wherein the adenosine $A_{2A}$ receptor antagonist is a compound represented by formula (XVII):

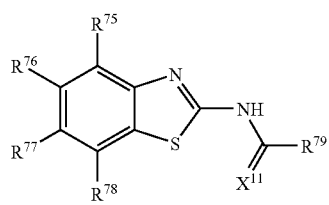

(XVII)

(wherein $R^{75}$ represents hydrogen, hydroxy, benzyloxy, halogen, substituted or unsubstituted lower alkyl, or substituted or unsubstituted lower alkoxy; $R^{76}$ and $R^{77}$ independently represent hydroxy, halogen, substituted or unsubstituted lower alkyl, or substituted or unsubstituted lower alkoxy; $R^{78}$ represents hydrogen, carboxy, halogen, substituted or unsubstituted lower alkyl, substituted or unsubstituted lower alkenyl, substituted or unsubstituted lower alkanoyl, substituted or unsubstituted lower alkoxycarbonyl, substituted or unsubstituted aryl, or a substituted or unsubstituted heterocyclic group; $R^{79}$ represents substituted or unsubstituted phenyl;

and —C(=X¹¹)— represents —C(=O)—, —C(=S)— or —CH₂—) {e.g. 4-hydroxymethyl-N-(4-methoxy-7-phenyl-benzothiazol-2-yl)benzamide}, or a pharmaceutically acceptable salt thereof.

(24) The method of treating an anxiety disorder according to the above (1) wherein the adenosine $A_{2A}$ receptor antagonist is (−)-(11S,2'R)-α-2-piperidinyl-2,8-bis(trifluoromethyl)-4-quinolinemethanol, or a pharmaceutically acceptable salt thereof.

(25) The method of treating an anxiety disorder according to the above (1) wherein the adenosine $A_{2A}$ receptor antagonist is a compound represented by formula (XII-A):

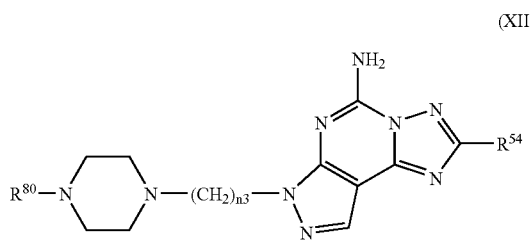

(XII-A)

(wherein $R^{54}$ has the same meaning as defined above; n3 is an integer of 1 to 4; and $R^{80}$ represents substituted or unsubstituted aryl, or a substituted or unsubstituted heterocyclic group) {e.g., 5-amino-2-(2-furyl)-7-(2-{4-[4-(2-methoxyethoxy)phenyl]piperazinyl}ethyl)pyrazolo[4,3-e]-1,2,4-triazolo[1,5-c]pyrimidine}, or a pharmaceutically acceptable salt thereof.

(26) The method of treating an anxiety disorder according to the above (1) wherein the adenosine $A_{2A}$ receptor antagonist is a compound represented by formula (XVIII):

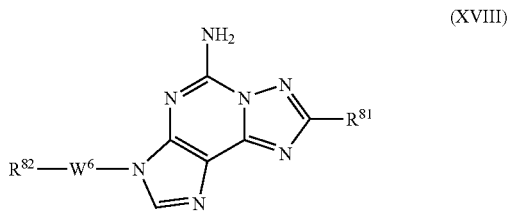

(XVIII)

(wherein $R^{81}$ represents substituted or unsubstituted aryl, substituted or unsubstituted cycloalkenyl, or substituted or unsubstituted heteroaryl; $W^6$ represents a single bond or —C(=O)—; and $R^{82}$ represents substituted or unsubstituted lower alkyl), or a pharmaceutically acceptable salt thereof.

(27) The method of treating an anxiety disorder according to the above (1) wherein the adenosine $A_{2A}$ receptor antagonist is a compound represented by formula (XVIII-A):

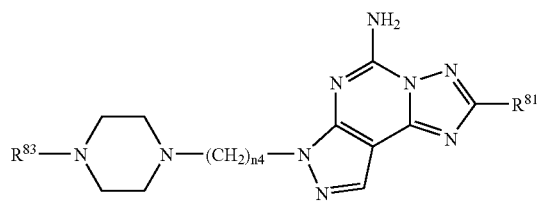

(XVIII-A)

(wherein $R^{81}$ has the same meaning as defined above; n4 is an integer of 1 to 4; and $R^{83}$ represents substituted or unsubstituted aryl, or a substituted or unsubstituted heterocyclic group) {e.g., 5-amino-2-(2-furyl)-7-(2-{4-[4-(2-methoxyethoxy)phenyl]piperazinyl}ethyl)imidazo[4,3-e]-1,2,4-triazolo[1,5-c]pyrimidine}, or a pharmaceutically acceptable salt thereof.

(28) The method of treating an anxiety disorder according to any one of the above (1) to (27), wherein the anxiety disorder is panic disorder.

(29) The method of treating an anxiety disorder according to any one of the above (1) to (27), wherein the anxiety disorder is agoraphobia.

(30) The method of treating an anxiety disorder according to any one of the above (1) to (27), wherein the anxiety disorder is obsessive-compulsive disorder.

(31) The method of treating an anxiety disorder according to any one of the above (1) to (27), wherein the anxiety disorder is social phobia.

(32) The method of treating an anxiety disorder according to any one of the above (1) to (27), wherein the anxiety disorder is post-traumatic stress disorder.

(33) The method of treating an anxiety disorder according to any one of the above (1) to (27), wherein the anxiety disorder is specific phobia.

(34) A method of treating an anxiety disorder, comprising administering an effective amount of a xanthine derivative represented by formula (I):

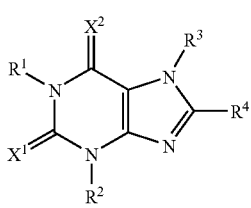

(I)

[wherein $R^1$, $R^2$ and $R^3$ independently represent hydrogen, lower alkyl, lower alkenyl or lower alkynyl; $R^4$ represents cycloalkyl, —(CH₂)ₙ—$R^5$ (in which $R^5$ represents substituted or unsubstituted aryl, or a substituted or unsubstituted heterocyclic group; and n is an integer of 0 to 4) or formula (I-i)

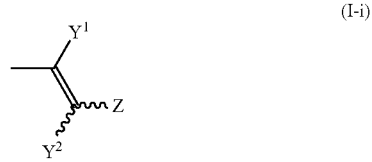

(I-i)

(in which $Y^1$ and $Y^2$ independently represent hydrogen, halogen or lower alkyl; and Z represents substituted or unsubstituted aryl, or a substituted or unsubstituted heterocyclic group); and $X^1$ and $X^2$ independently represent O or S], or a pharmaceutically acceptable salt thereof.

(35) The method of treating an anxiety disorder according to the above (34) wherein the xanthine derivative is a compound represented by formula (I-A):

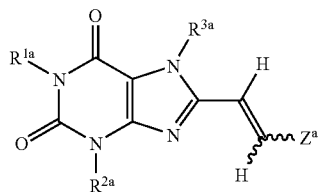

(I-A)

[wherein $R^{1a}$ and $R^{2a}$ independently represent methyl or ethyl; $R^{3a}$ represents hydrogen or lower alkyl; and $Z^a$ represents formula (I-ii)

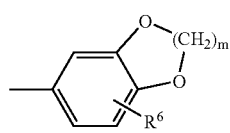

(I-ii)

(in which $R^6$ represents hydrogen, hydroxy, lower alkyl, lower alkoxy, halogen, nitro or amino; and m represents an integer of 1 to 3) or formula (I-iii)

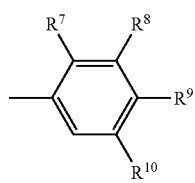

(I-iii)

(in which at least one of $R^7$, $R^8$ and $R^9$ represents lower alkyl or lower alkoxy and the others represent hydrogen; $R^{10}$ represents hydrogen or lower alkyl)], or a pharmaceutically acceptable salt thereof.

(36) The method of treating an anxiety disorder according to the above (34) wherein the xanthine derivative is a compound represented by formula (I-B):

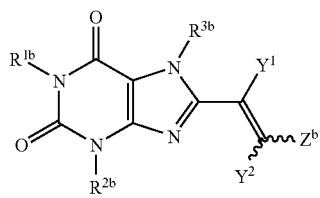

(I-B)

[wherein $R^{1b}$ and $R^{2b}$ independently represent hydrogen, propyl, butyl, lower alkenyl or lower alkynyl; $R^{3b}$ represents hydrogen or lower alkyl; $Z^b$ represents substituted or unsubstituted naphthyl, or formula (I-ii)

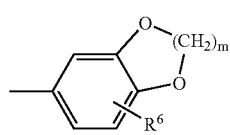

(I-ii)

(in which $R^6$ and m have the same meanings as defined above, respectively); and $Y^1$ and $Y^2$ have the same meanings as defined above, respectively], or a pharmaceutically acceptable salt thereof.

(37) The method of treating an anxiety disorder according to the above (34) wherein the xanthine derivative is (E)-8-(3,4-dimethoxystyryl)-1,3-diethyl-7-methylxanthine.

(38) The method of treating an anxiety disorder according to any one of the above (34) to (37), wherein the anxiety disorder is panic disorder.

(39) The method of treating an anxiety disorder according to any one of the above (34) to (37), wherein the anxiety disorder is agoraphobia.

(40) The method of treating an anxiety disorder according to any one of the above (34) to (37), wherein the anxiety disorder is obsessive-compulsive disorder.

(41) The method of treating an anxiety disorder according to any one of the above (34) to (37), wherein the anxiety disorder is social phobia.

(42) The method of treating an anxiety disorder according to any one of the above (34) to (37), wherein the anxiety disorder is post-traumatic stress disorder.

(43) The method of treating an anxiety disorder according to any one of the above (34) to (37), wherein the anxiety disorder is generalized anxiety disorder.

(44) The method of treating an anxiety disorder according to any one of the above (34) to (37), wherein the anxiety disorder is specific phobia.

(45) A method of treating an anxiety disorder, comprising administering an effective amount of at least one adenosine $A_{2A}$ receptor antagonist in combination with an anxiolytic other than the adenosine $A_{2A}$ receptor antagonist to a patient in need thereof.

(46) The method of treating an anxiety disorder according to the above (45) wherein the adenosine adenosine $A^{2A}$ receptor antagonist is a xanthine derivative or a pharmaceutically acceptable salt thereof.

(47) The method of treating an anxiety disorder according to the above (45) wherein the adenosine $A_{2A}$ receptor antagonist is a compound represented by formula (I):

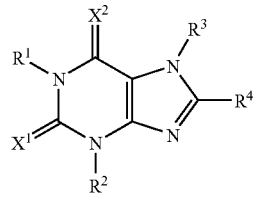

(I)

[wherein $R^1$, $R^2$ and $R^3$ independently represent hydrogen, lower alkyl, lower alkenyl or lower alkynyl; $R^4$ represents cycloalkyl, —$(CH_2)_n$—$R^5$ (in which $R^5$ represents substituted or unsubstituted aryl, or a substituted or unsubstituted heterocyclic group; and n is an integer of 0 to 4) or formula (I-i)

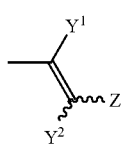

(I-i)

(in which $Y^1$ and $Y^2$ independently represent hydrogen, halogen or lower alkyl; and Z represents substituted or unsubstituted aryl, or a substituted or unsubstituted heterocyclic group); and $X^1$ and $X^2$ independently represent O or S], or a pharmaceutically acceptable salt thereof.

(48) The method of treating an anxiety disorder according to the above (45) wherein the adenosine $A_{2A}$ receptor antagonist is a compound represented by formula (I-A):

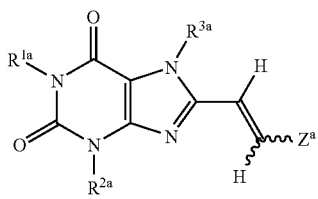
(I-A)

[wherein $R^{1a}$ and $R^{2a}$ independently represent methyl or ethyl; $R^{3a}$ represents hydrogen or lower alkyl; and $Z^a$ represents formula (I-ii)

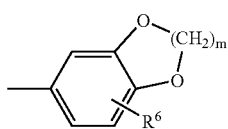
(I-ii)

(in which $R^6$ represents hydrogen, hydroxy, lower alkyl, lower alkoxy, halogen, nitro or amino; and m represents an integer of 1 to 3) or formula (I-iii)

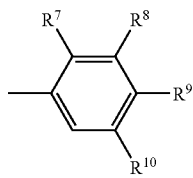
(I-iii)

(in which at least one of $R^7$, $R^8$ and $R^9$ represents lower alkyl or lower alkoxy and the others represent hydrogen; $R^{10}$ represents hydrogen or lower alkyl)], or a pharmaceutically acceptable salt thereof.

(49) The method of treating an anxiety disorder according to the above (45) wherein the adenosine $A_{2A}$ receptor antagonist is a compound represented by formula (I-B):

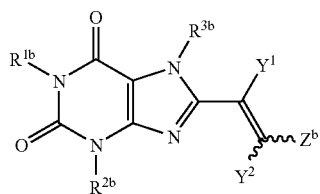
(I-B)

[wherein $R^{1b}$ and $R^{2b}$ independently represent hydrogen, propyl, butyl, lower alkenyl or lower alkynyl; $R^{3b}$ represents hydrogen or lower alkyl; $Z^b$ represents substituted or unsubstituted naphthyl, or formula (I-ii)

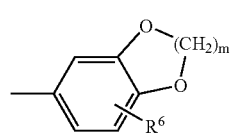
(I-ii)

(in which $R^6$ and m have the same meanings as defined above, respectively); and $Y^1$ and $Y^2$ have the same meanings as defined above, respectively], or a pharmaceutically acceptable salt thereof.

(50) The method of treating an anxiety disorder according to the above (45) wherein the adenosine $A_{2A}$ receptor antagonist is (E)-8-(3,4-dimethoxystyryl)-1,3-diethyl-7-methylxanthine.

(51) The method of treating an anxiety disorder according to any one of the above (45) to (50), wherein the anxiety disorder is panic disorder, agoraphobia, obsessive-compulsive disorder, social phobia, post-traumatic stress disorder, generalized anxiety disorder or specific phobia.

(52) A composition comprising an adenosine $A_{2A}$ receptor antagonist and an anxiolytic other than the adenosine $A_{2A}$ receptor antagonist.

(53) The composition according to the above (52) wherein the adenosine adenosine $A_{2A}$ receptor antagonist is a xanthine derivative or a pharmaceutically acceptable salt thereof.

(54) The composition according to the above (52) wherein the adenosine $A_{2A}$ receptor antagonist is a compound represented by formula (I):

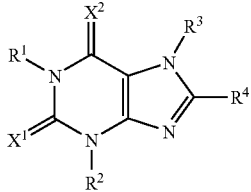
(I)

(wherein $R^1$, $R^2$ and $R^3$ independently represent hydrogen, lower alkyl, lower alkenyl or lower alkynyl; $R^4$ represents cycloalkyl, —$(CH_2)_n$—$R^5$ (in which $R^5$ represents substituted or unsubstituted aryl, or a substituted or unsubstituted heterocyclic group; and n is an, integer of 0 to 4) or formula (I-i)

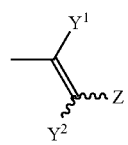
(I-i)

(in which $Y^1$ and $Y^2$ independently represent hydrogen, halogen or lower alkyl; and Z represents substituted or unsubstituted aryl, or a substituted or unsubstituted heterocyclic group); and $X^1$ and $X^2$ independently represent O or S], or a pharmaceutically acceptable salt thereof.

(55) The composition according to the above (52) wherein the adenosine $A_{2A}$ receptor antagonist is a compound represented by formula (I-A):

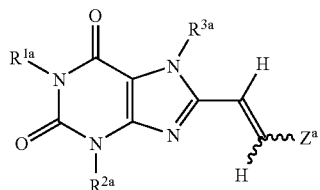

(I-A)

[wherein $R^{1a}$ and $R^{2a}$ independently represent methyl or ethyl; $R^{3a}$ represents hydrogen or lower alkyl; and $Z^a$ represents formula (I-ii)

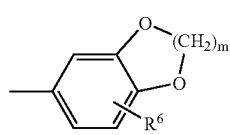

(I-ii)

(in which $R^6$ represents hydrogen, hydroxy, lower alkyl, lower alkoxy, halogen, nitro or amino; and m represents an integer of 1 to 3) or formula (I-iii)

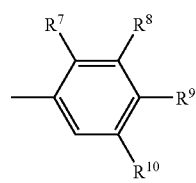

(I-iii)

(in which at least one of $R^7$, $R^8$ and $R^9$ represents lower alkyl or lower alkoxy and the others represent hydrogen; $R^{10}$ represents hydrogen or lower alkyl)], or a pharmaceutically acceptable salt thereof.

(56) The composition according to the above (52) wherein the adenosine $A_{2A}$ receptor antagonist is a compound, represented by formula (I-B):

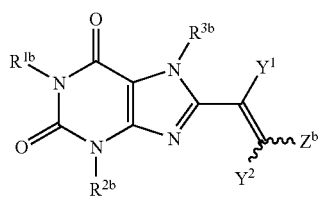

(I-B)

[wherein $R^{1b}$ and $R^{2b}$ independently represent hydrogen, propyl, butyl, lower alkenyl or lower alkynyl; $R^{3b}$ represents hydrogen or lower alkyl; $Z^b$ represents substituted or unsubstituted naphthyl, or formula (I-ii)

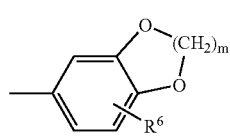

(I-ii)

(in which $R^6$ and m have the same meanings as defined above, respectively); and $Y^1$ and $Y^2$ have the same meanings as defined above, respectively], or a pharmaceutically acceptable salt thereof.

(57) The composition according to the above (52) wherein the adenosine $A_{2A}$ receptor antagonist is (E)-8-(3,4-dimethoxystyryl)-1,3-diethyl-7-methylxanthine, or a pharmaceutically acceptable salt thereof.

(58) The method of treating an anxiety disorder according to the above (1) wherein the adenosine $A_{2A}$ receptor antagonist is a triazolopyrimidine derivative or a pharmaceutically acceptable salt thereof.

(59) An agent for treating an anxiety disorder selected from the group consisting of panic disorder, agoraphobia, obsessive-compulsive disorder, social phobia, post-traumatic stress disorder, and specific phobia, comprising a compound having adenosine $A_{2A}$ receptor antagonistic activity or a pharmaceutically acceptable salt thereof as an active ingredient.

(60) The agent for treating an anxiety disorder according to the above (59) wherein the compound having adenosine $A_{2A}$ receptor antagonistic activity is a xanthine derivative or a pharmaceutically acceptable salt thereof.

(61) The agent for treating an anxiety disorder according to the above (59) wherein the compound having adenosine $A_{2A}$ receptor antagonistic activity is a compound represented by formula (I):

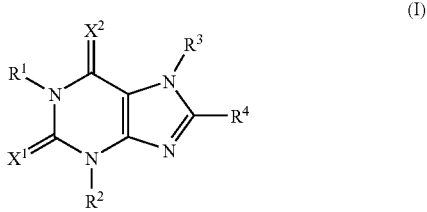

(I)

[wherein $R^1$, $R^2$ and $R^3$ independently represent hydrogen, lower alkyl, lower alkenyl or lower alkynyl; $R^4$ represents cycloalkyl, —$(CH_2)_n$—$R^5$ (in which $R^5$ represents substituted or unsubstituted aryl, or a substituted or unsubstituted heterocyclic group; and n is an integer of 0 to 4) or formula (I-i)

(I-i)

(in which $Y^1$ and $Y^2$ independently represent hydrogen, halogen or lower alkyl; and Z represents substituted or unsubstituted aryl, or a substituted or unsubstituted heterocyclic group); and $X^1$ and $X^2$ independently represent O or S], or a pharmaceutically acceptable salt thereof.

(62) The agent for treating an anxiety disorder according to the above (59) wherein the compound having adenosine $A_{2A}$ receptor antagonistic activity is a compound represented by formula (I-A):

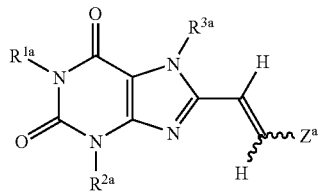

(I-A)

[wherein $R^{1a}$ and $R^{2a}$ independently represent methyl or ethyl; $R^{3a}$ represents hydrogen or lower alkyl; and $Z^a$ represents formula (I-ii)

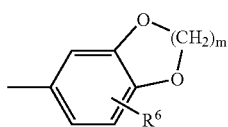

(I-ii)

(in which $R^6$ represents hydrogen, hydroxy, lower alkyl, lower alkoxy, halogen, nitro or amino; and m represents an integer of 1 to 3) or formula (I-iii)

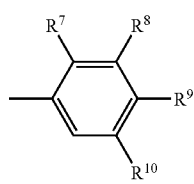

(I-iii)

(in which at least one of $R^7$, $R^8$ and $R^9$ represents lower alkyl or lower alkoxy and the others represent hydrogen; $R^{10}$ represents hydrogen or lower alkyl)], or a pharmaceutically acceptable salt thereof.

(63) The agent for treating an anxiety disorder according to the above (59) wherein the compound having adenosine $A_{2A}$ receptor antagonistic activity is a compound represented by formula (I-B):

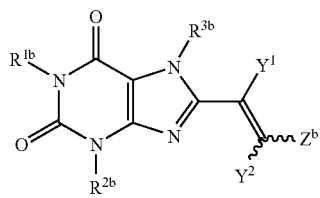

(I-B)

[wherein $R^{1b}$ and $R^{2b}$ independently represent hydrogen, propyl, butyl, lower alkenyl or lower alkynyl; $R^{3b}$ represents hydrogen or lower alkyl; $Z^b$ represents substituted or unsubstituted naphthyl, or formula (I-ii)

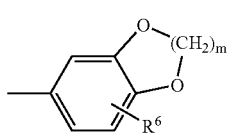

(I-ii)

(in which $R^6$ and m have the same meanings as defined above, respectively); and $Y^1$ and $Y^2$ have the same meanings as defined above, respectively], or a pharmaceutically acceptable salt thereof.

(64) The agent for treating an anxiety disorder according to the above (59) wherein the compound having adenosine $A_{2A}$ receptor antagonistic activity is (E)-8-(3,4-dimethoxystyryl)-1,3-diethyl-7-methylxanthine or a pharmaceutically acceptable salt thereof.

(65) The agent for treating an anxiety disorder according to the above (59) wherein the compound having adenosine $A_{2A}$ receptor antagonistic activity is a triazolopyrimidine derivative or a pharmaceutically acceptable salt thereof.

(66) The agent for treating an anxiety disorder according to the above (59) wherein the compound having adenosine $A_{2A}$ receptor antagonistic activity is a compound represented by formula (II):

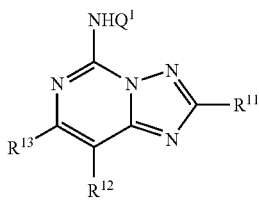

(II)

[wherein $R^{11}$ represents substituted or unsubstituted aryl, or a substituted or unsubstituted heterocyclic group; $R^{12}$ represents hydrogen, halogen, substituted or unsubstituted lower alkyl, substituted or unsubstituted aryl, or a substituted or unsubstituted heterocyclic group; $R^{13}$ represents hydrogen, halogen or —$WR^{14}$ (in which W represents —O— or —S—; and $R^{14}$ represents substituted or unsubstituted lower alkyl, substituted or unsubstituted aryl, or a substituted or unsubstituted heterocyclic group); and $Q^1$ represents hydrogen or 3,4-dimethoxybenzyl] {e.g. 5-amino-7-(4-benzoylpiperazinyl)-2-(2-furyl)[1,2,4]triazolo[1,5-c]pyrimidine}, or a pharmaceutically acceptable salt thereof.

(67) The agent for treating an anxiety disorder according to the above (59) wherein the compound having adenosine $A_{2A}$ receptor antagonistic activity is a compound represented by formula (III):

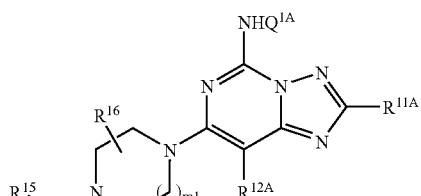

(III)

[wherein $R^{11A}$ represents substituted or unsubstituted aryl, or substituted or unsubstituted heteroaryl; $R^{12A}$ represents hydrogen, halogen, substituted or unsubstituted lower alkyl, substituted or unsubstituted aryl, or substituted or unsubstituted heteroaryl; m1 and n1 are independently an integer of 0 to 4; $Q^{1A}$ represents hydrogen or 3,4-dimethoxybenzyl; $R^{15}$ represents hydrogen, substituted or unsubstituted aryl, a substituted or unsubstituted heterocyalic group, or —$CR^{17}R^{18}R^{19}$ (in which $R^{17}$, $R^{18}$ and $R^{19}$ independently represent hydrogen, hydroxy, substituted or unsubstituted lower alkyl, substituted or unsubstituted lower alkoxy, substituted or unsubstituted aryl, or a substituted or unsubstituted heterocyalic group; or $R^{18}$ and $R^{19}$ are combined together with an adjacent carbon atom to form a substituted or unsubstituted carbon ring); and $R^{16}$ represents hydrogen, halogen, hydroxy, or substituted or unsubstituted lower alkyl], or a pharmaceutically acceptable salt thereof.

(68) The agent for treating an anxiety disorder according to the above (59) wherein the compound having adenosine $A_{2A}$ receptor antagonistic activity is a compound represented by formula (III-A):

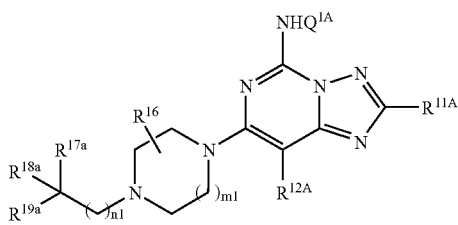

(III-A)

(wherein $Q^{1A}$, $R^{11A}$, $R^{12A}$, $R^{16}$, m1 and n1 have the same meanings as defined above, respectively; $R^{17a}$ represents hydroxy, hydroxyl-substituted lower alkyl, substituted or unsubstituted lower alkoxy, or imidazo[1,2-a]pyridyl; and $R^{18a}$ and $R^{19a}$ independently represent hydrogen, substituted or unsubstituted lower alkyl, or substituted or unsubstituted aryl; or $R^{18a}$ and $R^{19a}$ are combined together with an adjacent carbon atom to form a substituted or unsubstituted carbon ring) {e.g. 5-amino-2-(2-furyl)-7-[4-(2-hydroxy-2-methylpropyl)piperazinyl][1,2,4]triazolo[1,5-c]pyrimidine, and 5-amino-2-(2-furyl)-7-[4-(3-hydroxy-3-methylbutyl)piperazinyl][1,2,4]triazolo[1,5-c]pyrimidine}, or a pharmaceutically acceptable salt thereof.

(69) The agent for treating an anxiety disorder according to the above (59) wherein the compound having adenosine $A_{2A}$ receptor antagonistic activity is a compound represented by formula (XII):

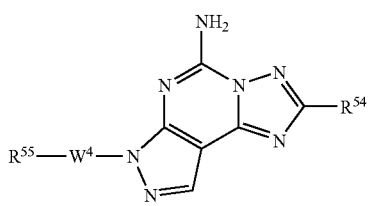

(XII)

(wherein $R^{54}$ represents substituted or unsubstituted aryl, substituted or unsubstituted cycloalkenyl, or substituted or unsubstituted heteroaryl; $W^4$ represents a single bond or —C(=O)—; and $R^{55}$ represents substituted or unsubstituted lower alkyl), or a pharmaceutically acceptable salt thereof.

(70) The agent for treating an anxiety disorder according to the above (59) wherein the compound having adenosine $A_{2A}$ receptor antagonistic activity is a compound represented by formula (XII-A):

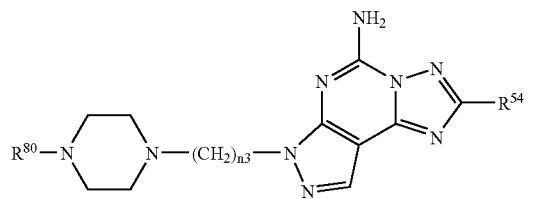

(XII-A)

(wherein $R^{54}$ has the same meaning as defined above; n3 is an integer of 1 to 4; and $R^{80}$ represents substituted or unsubstituted aryl, or a substituted or unsubstituted heterocyclic group) {e.g., 5-amino-2-(2-furyl)-7-(2-{4-[4-(2-methoxyethoxy)phenyl]piperazinyl}ethyl)pyrazolo[4,3-e]-1,2,4-triazolo[1,5-c]pyrimidine}, or a pharmaceutically acceptable salt thereof.

(71) The agent for treating an anxiety disorder according to the above (59) wherein the compound having adenosine $A_{2A}$ receptor antagonistic activity is a compound represented by formula (XVIII):

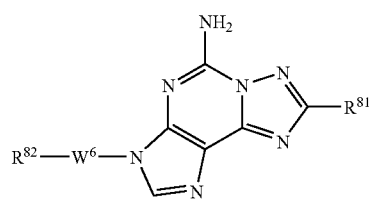

(XVIII)

(wherein $R^{81}$ represents substituted or unsubstituted aryl, substituted or unsubstituted cycloalkenyl, or substituted or unsubstituted heteroaryl; $W^6$ represents a single bond or —C(=O)—; and $R^{82}$ represents substituted or unsubstituted lower alkyl), or a pharmaceutically acceptable salt thereof.

(72) The agent for treating an anxiety disorder according to the above (59) wherein the compound having adenosine $A_{2A}$ receptor antagonistic activity is a compound represented by formula (XVIII-A):

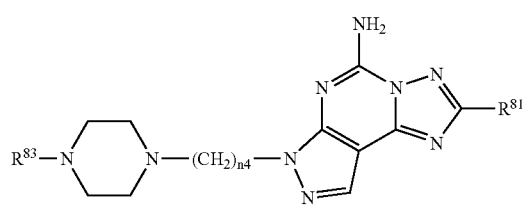

(XVIII-A)

(wherein $R^{81}$ has the same meaning as defined above; n4 is an integer of 1 to 4; and $R^{83}$ represents substituted or unsubstituted aryl, or a substituted or unsubstituted heterocyclic group) {e.g., 5-amino-2-(2-furyl)-7-(2-{4-[4-(2-methoxyethoxy)phenyl]piperazinyl}ethyl)imidazo[4,3-e]-1,2,4-triazolo[1,5-c]pyrimidine}, or a pharmaceutically acceptable salt thereof.

(73) An agent for treating an anxiety disorder, comprising a xanthine derivative represented by formula (I):

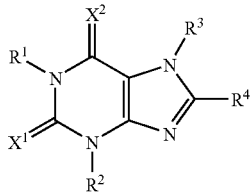

(wherein $R^1$, $R^2$ and $R^3$ independently represent hydrogen, lower alkyl, lower alkenyl or lower alkynyl; $R^4$ represents cycloalkyl, $-(CH_2)_n-R^5$ (in which $R^5$ represents substituted or unsubstituted aryl, or a substituted or unsubstituted heterocyclic group; and n is an integer of 0 to 4) or formula (I-i)

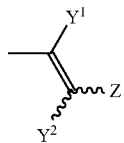

(in which $Y^1$ and $Y^2$ independently represent hydrogen, halogen or lower alkyl; and Z represents substituted or unsubstituted aryl, or a substituted or unsubstituted heterocyclic group); and $X^1$ and $X^2$ independently represent O or S], or a pharmaceutically acceptable salt thereof as an active ingredient.

(74) Use of a compound having adenosine $A_{2A}$ receptor antagonistic activity or a pharmaceutically acceptable salt thereof for the manufacture of an agent for treating an anxiety disorder selected from the group consisting of panic disorder, agoraphobia, obsessive-compulsive disorder, social phobia, post-traumatic stress disorder, and specific phobia.

(75) The use according to the above (74) wherein the compound having adenosine $A_{2A}$ receptor antagonistic activity is a xanthine derivative or a pharmaceutically acceptable salt thereof.

(76) The use according to the above (74) wherein the compound having adenosine $A_{2A}$ receptor antagonistic activity is a compound represented by formula (I):

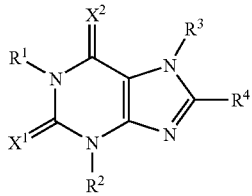

[wherein $R^1$, $R^2$ and $R^3$ independently represent hydrogen, lower alkyl, lower alkenyl or lower alkynyl; $R^4$ represents cycloalkyl, $-(CH_2)_n-R^5$ (in which $R^5$ represents substituted or unsubstituted aryl, or a substituted or unsubstituted heterocyclic group; and n is an integer of 0 to 4) or formula (I-i)

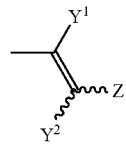

(in which $Y^1$ and $Y^2$ independently represent hydrogen, halogen or lower alkyl; and Z represents substituted or unsubstituted aryl, or a substituted or unsubstituted heterocyclic group); and $X^1$ and $X^2$ independently represent O or S], or a pharmaceutically acceptable salt thereof.

(77) The use according to the above (74) wherein the compound having adenosine $A_{2A}$ receptor antagonistic activity is a compound represented by formula (I-A):

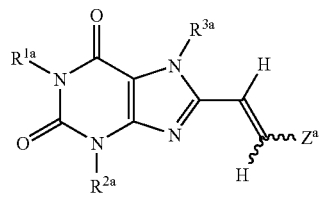

[wherein $R^{1a}$ and $R^{2a}$ independently represent methyl or ethyl; $R^{3a}$ represents hydrogen or lower alkyl; and $Z^a$ represents formula (I-ii)

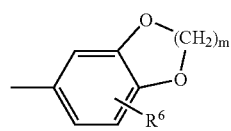

(in which $R^6$ represents hydrogen, hydroxy, lower alkyl, lower alkoxy, halogen, nitro or amino; and m represents an integer of 1 to 3) or formula (I-iii)

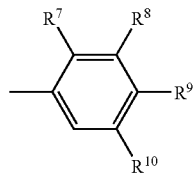

(in which at least one of $R^7$, $R^8$ and $R^9$ represents lower alkyl or lower alkoxy and the others represent hydrogen; $R^{10}$ represents hydrogen or lower alkyl)], or a pharmaceutically acceptable salt thereof.

(78) The use according to the above (74) wherein the compound having adenosine $A_{2A}$ receptor antagonistic activity is a compound represented by formula (I-B):

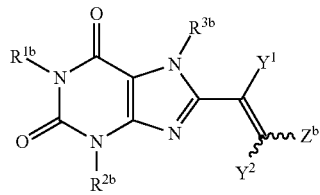

(I-B)

[wherein $R^{1b}$ and $R^{2b}$ independently represent hydrogen, propyl, butyl; lower alkenyl or lower alkynyl; $R^{3b}$ represents hydrogen or lower alkyl; $Z^b$ represents substituted or unsubstituted naphthyl, or formula (I-ii)

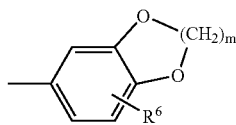

(I-ii)

(in which $R^6$ and m have the same meanings as defined above, respectively); and $Y^1$ and $Y^2$ have the same meanings as defined above, respectively], or a pharmaceutically acceptable salt thereof.

(79) The use according to the above (74) wherein the compound having adenosine $A_{2A}$ receptor antagonistic activity is (E)-8-(3,4-dimethoxystyryl)-1,3-diethyl-7-methylxanthine or a pharmaceutically acceptable salt thereof.

(80) The use according to the above (74) wherein the compound having adenosine $A_{2A}$ receptor antagonistic activity is a triazolopyrimidine derivative or a pharmaceutically acceptable salt thereof.

(81) The use according to the above (74) wherein the compound having adenosine $A_{2A}$ receptor antagonistic activity is a compound represented by formula (II):

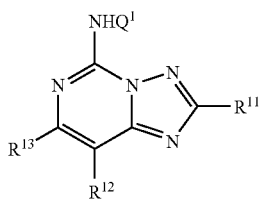

(II)

[wherein $R^{11}$ represents substituted or unsubstituted aryl, or a substituted or unsubstituted heterocyclic group; $R^{12}$ represents hydrogen, halogen, substituted or unsubstituted lower alkyl, substituted or unsubstituted aryl, or a substituted or unsubstituted heterocyclic group; $R^{13}$ represents hydrogen, halogen or —$WR^{14}$ (in which W represents —O— or —S—; and $R^{14}$ represents substituted or unsubstituted lower alkyl, substituted or unsubstituted aryl, or a substituted or unsubstituted heterocyclic group); and $Q^1$ represents hydrogen or 3,4-dimethoxybenzyl] {e.g. 5-amino-7-(4-benzoylpiperazinyl)-2-(2-furyl)[1,2,4]triazolo[1,5-c]pyrimidine}, or a pharmaceutically acceptable salt thereof.

(82) The use according to the above (74) wherein the compound having adenosine $A_{2A}$ receptor antagonistic activity is a compound represented by formula (III):

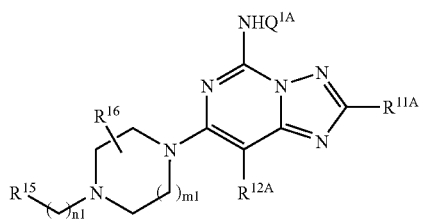

(III)

[wherein $R^{11A}$ represents substituted or unsubstituted aryl, or substituted or unsubstituted heteroaryl; $R^{12A}$ represents hydrogen, halogen, substituted or unsubstituted lower alkyl, substituted or unsubstituted aryl, or substituted or unsubstituted heteroaryl; m1 and n1 are independently an integer of 0 to 4; $Q^{1A}$ represents hydrogen or 3,4-dimethoxybenzyl; $R^{15}$ represents hydrogen, substituted or unsubstituted aryl, a substituted or unsubstituted heterocyalic group, or —$CR^{17}R^{18}R^{19}$ (in which $R^{17}$, $R^{18}$ and $R^{19}$ independently represent hydrogen, hydroxy, substituted or unsubstituted lower alkyl, substituted or unsubstituted lower alkoxy, substituted or unsubstituted aryl, or a substituted or unsubstituted heterocyalic group; or $R^{18}$ and $R^{19}$ are combined together with an adjacent carbon atom to form a substituted or unsubstituted carbon ring); and $R^{16}$ represents hydrogen, halogen, hydroxy, or substituted or unsubstituted lower alkyl], or a pharmaceutically acceptable salt thereof.

(83) The use according to the above (74) wherein the compound having adenosine $A_{2A}$ receptor antagonistic activity is a compound represented by formula (III-A):

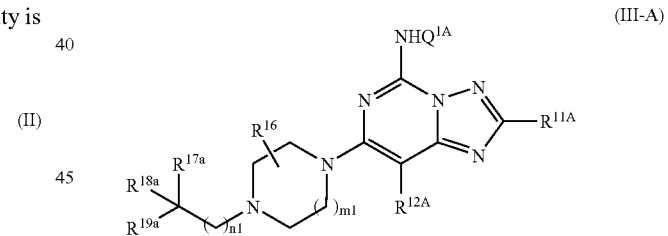

(III-A)

(wherein $Q^{1A}$, $R^{11A}$, $R^{12A}$, $R^{16}$, m1 and n1 have the same meanings as defined above, respectively; $R^{17a}$ represents hydroxy, hydroxyl-substituted lower alkyl, substituted or unsubstituted lower alkoxy, or imidazo[1,2-a]pyridyl; and $R^{18a}$ and $R^{19a}$ independently represent hydrogen, substituted or unsubstituted lower alkyl, or substituted or unsubstituted aryl; or $R^{18a}$ and $R^{19a}$ are combined together with an adjacent carbon atom to form a substituted or unsubstituted carbon ring) {e.g. 5-amino-2-(2-furyl)-7-[4-(2-hydroxy-2-methylpropyl)piperazinyl][1,2,4]triazolo[1,5-c]pyrimidine, and 5-amino-2-(2-furyl)-7-[4-(3-hydroxy-3-methylbutyl)piperazinyl][1,2,4]triazolo[1,5-c]pyrimidine}, or a pharmaceutically acceptable salt thereof.

(84) The use according to the above (74) wherein the compound having adenosine $A_{2A}$ receptor antagonistic activity is a compound represented by formula (XII):

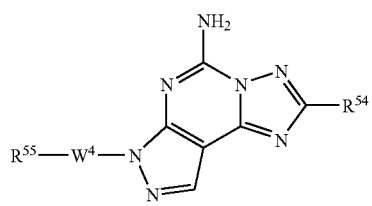

(XII)

(wherein R$^{54}$ represents substituted or unsubstituted aryl, substituted or unsubstituted cycloalkenyl, or substituted or unsubstituted heteroaryl; W$^4$ represents a single bond or —C(=O)—; and R$^{55}$ represents substituted or unsubstituted lower alkyl), or a pharmaceutically acceptable salt thereof.

(85) The use according to the above (74) wherein the compound having adenosine A$_{2A}$ receptor antagonistic activity is a compound represented by formula (XII-A):

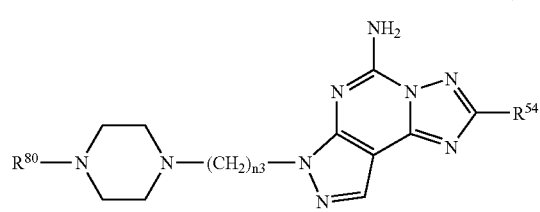

(XII-A)

(wherein R$^{54}$ has the same meaning as defined above; n3 is an integer of 1 to 4; and R$^{80}$ represents substituted or unsubstituted aryl, or a substituted or unsubstituted heterocyclic group) {e.g., 5-amino-2-(2-furyl)-7-(2-{4-[4-(2-methoxyethoxy)phenyl]piperazinyl}ethyl)pyrazolo[4,3-e]-1,2,4-triazolo[1,5-c]pyrimidine}, or a pharmaceutically acceptable salt thereof.

(86) The use according to the above (74) wherein the compound having adenosine A$_{2A}$ receptor antagonistic activity is a compound represented by formula (XVIII):

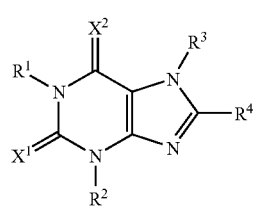

(XVIII)

(wherein R$^{81}$ represents substituted or unsubstituted aryl, substituted or unsubstituted cycloalkenyl, or substituted or unsubstituted heteroaryl; W$^6$ represents a single bond or —C(=O)—; and R$^{82}$ represents substituted or unsubstituted lower alkyl), or a pharmaceutically acceptable salt thereof.

(87) The use according to the above (74) wherein the compound having adenosine A$_{2A}$ receptor antagonistic activity is a compound represented by formula (XVIII-A):

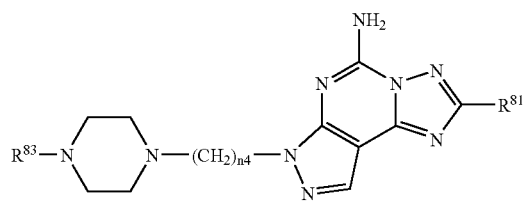

(XVIII-A)

(wherein R$^{81}$ has the same meaning as defined above; n4 is an integer of 1 to 4; and R$^{83}$ represents substituted or unsubstituted aryl, or a substituted or unsubstituted heterocyclic group) {e.g., 5-amino-2-(2-furyl)-7-(2-{4-[4-(2-methoxyethoxy)phenyl]piperazinyl}ethyl)imidazo[4,3-e]-1,2,4-triazolo[1,5-c]pyrimidine}, or a pharmaceutically acceptable salt thereof.

(88) Use of a xanthine deriative represented by formula (I):

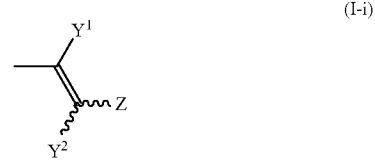

(I)

[wherein R$^1$, R$^2$ and R$^3$ independently represent hydrogen, lower alkyl, lower alkenyl or lower alkynyl; R$^4$ represents cycloalkyl, —(CH$_2$)$_n$—R$^5$ (in which R$^5$ represents substituted or unsubstituted aryl, or a substituted or unsubstituted heterocyclic group; and n is an integer of 0 to 4) or formula (I-i)

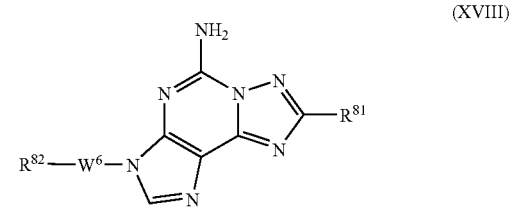

(I-i)

(in which Y$^1$ and Y$^2$ independently represent hydrogen, halogen or lower alkyl; and Z represents substituted or unsubstituted aryl, or a substituted or unsubstituted heterocyclic group); and X$^1$ and X$^2$ independently represent O or S], or a pharmaceutically acceptable salt thereof for the manufacture of an agent for treating an anxiety disorder.

The anxiety disorder includes panic disorder, agoraphobia, obsessive-compulsive disorder, social phobia, post-traumatic stress disorder, generalized anxiety disorder, specific phobia, and other anxiety disorders.

The adenosine A$_{2A}$ receptor antagonist used in the method of the present invention is not limited as long as it has A$_{2A}$ receptor antagonistic activity, including xanthine derivatives, triazolopyrimidine derivatives such as [1,2,4]triazolo[1,5-c]pyrimidine dertivatives, [1,2,4]triazolo[1,5-a]pyrimidine derivatives, pyrazolo[4,3-e]-1,2,4-triazolo[1,5-c]pyrimidine dertivatives and imidazo[4,3-e]-1,2,4-triazolo[1,5-c]pyrimidine dertivatives, and pharmaceutically acceptable salts thereof. A$_{2A}$ receptor antagonistic activity includes activity to inhibit, suppress or cause the cessation of at least one adenosine-mediated biological activity by, e.g., binding to adenosine A$_{2A}$ receptors, or interfering with or preventing the binding of adenosine to the receptor. Examples of known adenosine A$_{2A}$ receptor antagonist include compounds disclosed in U.S. Pat. No. 5,484,920, U.S. Pat. No. 5,703,085, WO 92/06976, WO 94/01114, U.S. Pat. No. 5,565,460, WO 98/42711, WO 00/17201, WO 99/43678, WO 99/26627, WO 01/92264, WO 99/35147, WO 00/13682, WO 00/13681, WO 00/69464, WO 01/40230, WO 01/02409, WO 01/02400, EP 1054012, WO 01/62233, WO 01/17999, WO 01/80893, WO 02/14282, WO 01/97786, WO 03/032996, WO 03/048163, WO 03/048164, WO 03/048165, or the like. More specifically, examples include compounds represented by the above-described formulas (I), (I-A), (I-B), (II), (III), (III-A), (IV) to (XII), (XII-A), (XIII) to (XVIII) or (XVIII-A), (−)-(11S, 2'R)-α-2-piperidinyl-2,8-bis(trifluoromethyl)-4-quinolinemethanol, and pharmaceutically acceptable salts thereof.

A preferred adenosine $A_{2A}$ receptor antagonist used in the method of the present invention is (E)-8-(3,4-dimethoxystyryl)-1,3-diethyl-7-methylxanthine (hereinafter referred to Compound A) shown below.

(A)
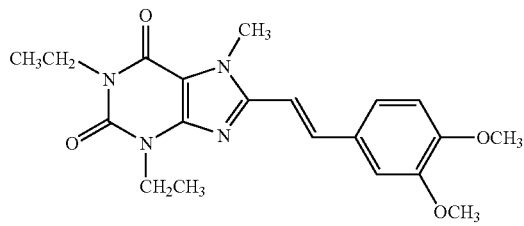

Another preferred adenosine $A_{2A}$ receptor antagonist used in the method of the present invention is (E)-1,3,7-trimethyl-8-(3,4,5-trimethoxystyryl)xanthine (hereinafter referred to Compound B) shown below.

(B)
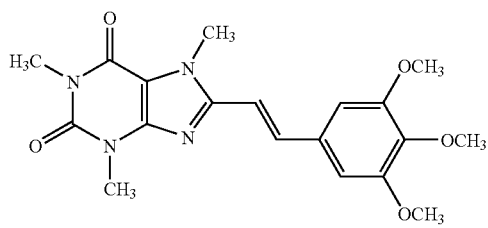

Another preferred adenosine $A_{2A}$ receptor antagonist used in the method of the present invention is 5-amino-2-(2-furyl)-7-[4-(3-hydroxy-3-methylbutyl)piperazinyl][1,2,4]triazolo[1,5-c]pyrimidine (hereinafter referred to Compound C) shown below.

(C)
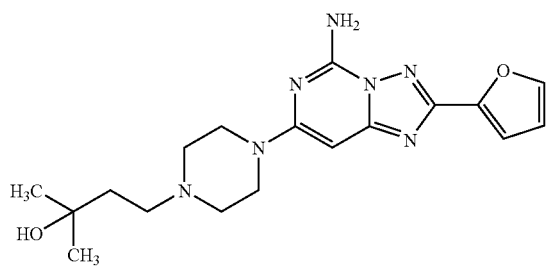

Another preferred adenosine $A_{2A}$ receptor antagonist used in the method of the present invention is 5-amino-2-(2-furyl)-7-(2-{4-[4-(2-methoxyethoxy)phenyl]piperazinyl}ethyl)pyrazolo[4,3-e]-1,2,4-triazolo[1,5-c]pyrimidine (hereinafter referred to Compound D) shown below.

(D)
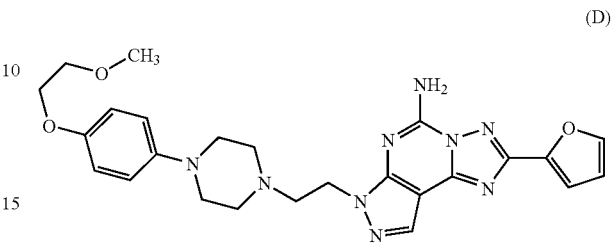

In the definition of each group in formula (I), (I-A), (I-B), (I-i), (I-ii), (I-iii), (II), (III), (III-A), (IV) to (XII), (XII-A), (XIII) to (XVIII) and (XVIII-A):

The lower alkyl, and the lower alkyl moiety of the lower alkoxy, the hydroxy-substituted lower alkyl, the lower alkanoyl and the lower alkoxycarbonyl include straight-chain or branched alkyl groups having 1 to 8 carbon atoms, such as methyl, ethyl, propyl, isopropyl, butyl, isobutyl, sec-butyl, tert-butyl, pentyl, neopentyl, hexyl, heptyl and octyl.

The lower alkenyl includes straight-chain or branched alkenyl groups having 2 to 8 carbon atoms, such as vinyl, allyl, methacryl, crotyl, 3-butenyl, 2-pentenyl, 4-pentenyl, 2-hexenyl, 5-hexenyl, 2-heptenyl and 2-octenyl.

The lower alkynyl includes straight-chain or branched alkynyl groups having 2 to 8 carbon atoms, such as ethynyl, propargyl, 2-butynyl, 3-butynyl, 2-pentynyl, 4-pentynyl, 2-hexynyl, 5-hexynyl, 4-methyl-2-pentynyl, 2-heptynyl and 2-octynyl.

The cycloalkyl includes cycloalkyl groups having 3 to 8 carbon atoms, such as cyclopropyl, cyclobutyl, cyclopentyl, cyclohexyl, cycloheptyl and cyclooctyl.

The cycloalkenyl includes cycloalkenyl groups having 4 to 8 carbon atoms, such as cyclobutenyl, cyclopentenyl, cyclohexenyl, cycloheptenyl and cyclooctenyl.

The aryl includes those having 6 to 14 carbon atoms, such as phenyl and naphthyl.

Examples of the heteroaryl are pyridyl, pyrazinyl, pyrimidinyl, pyridazinyl, pyridazinonyl, quinolyl, isoquinolyl, phthalazinyl, quinazolinyl, quinoxalinyl, naphthyridinyl, cinnolinyl, pyrrolyl, pyrazolyl, imidazolyl, triazinyl, triazolyl, tetrazolyl, thienyl, furyl, thiazolyl, isothiazolyl, oxazolyl, isooxazolyl, oxadiazolyl, thiadiazolyl, oxooxadiazolyl, indolyl, isoindolyl, indazolyl, benzimidazolyl, benzotriazolyl, benzothiazolyl, benzoxazolyl, 2-oxobenzimidazolyl, benzofuryl, benzothienyl, purinyl, dibenzofuranyl and imidazo[1,2-a]pyridyl.

Examples of the heterocyclic group are pyranyl, thiopyranyl, pyrrolidinyl, piperidino, piperazinyl, piperidinyl, imidazolidinyl, thiazolidinyl, morpholino, morpholinyl, thiomorpholino, thiomorpholinyl, homopiperidino, homopiperidinyl, homopiperazinyl, tetrahydropyridinyl, dihydroisoquinolyl, tetrahydroquinolyl, tetrahydroisoquinolyl, oxazolinyl, oxazolidinyl, oxooxazolidinyl, oxadiazolinyl, oxolanyl, tetrahydrofuranyl, tetrahydropyranyl, dihydrobenzofuranyl, oxopiperazinyl, oxopyrrolidinyl, dioxolanyl, 1,3-benzodioxolyl, 1,4-benzodioxanyl, 3,4-dihydo-2H-1,5-benzodioxepinyl, benzopyranyl, benzodihydropyranyl, perhydrodiazepinyl and perhydrodiazocinyl in addition to groups listed as examples of the heteroaryl. Examples of the alicyclic heterocyclic group include The halogen includes fluorine, chlorine, bromine and iodine.

The carbon ring formed by combining A and the adjacent two carbon atoms includes those having 4 to 8 carbon atoms and at least one double bond, such as cyclobutene, cyclopentene, cyclohexene, cycloheptene and cyclooctene.

Examples of the heterocyclic ring formed by combining A and the adjacent two carbon atoms are pyrrole, pyrane, thiopyrane, pyridine, thiazole, imidazole, pyrimidine, triazine, indole, quinoline, benzothiazole, pyrroline, tetrahydropyridine, tetrahydropyrazine, tetrahydroquinoline and tetrahydroisoquinoline.

The carbon ring formed together with the adjacent carbon atom includes cycloalkane and cycloalkene having 4 to 8 carbon atoms, such as cyclobutane, cyclopentane, cyclohexane, cycloheptane, cyclooctane, cyclobutene, cyclopentene, cyclohexene, cycloheptene and cyclooctene.

The substituted lower alkyl, the substituted lower alkoxy, the substituted lower alkanoyl, the substituted lower alkoxycarbonyl, the substituted lower alkenyl and the substituted lower alkynyl each have 1 to 3 independently selected substituents (A). Examples of the substituents (A) are hydroxy, cyano, nitro, carboxy, carbamoyl, amino, benzyloxy, phenoxy, halogen, trifluoromethyl, trifluoromethoxy, substituted or unsubstituted lower alkoxy, cycloalkyl, lower alkanoyl, lower alkoxycarbonyl, lower alkylamino, di(lower alkyl)amino, substituted or unsubstituted aryl and a substituted or unsubstituted heterocyalic group. In the examples of the substituents (A), the alkyl moiety of the lower alkoxy, the lower alkanoyl, the lower alkoxycarbonyl, the lower alkylamino and the di(lower alkyl)amino (two lower alkyl moieties of the di(lower alkyl)amino may be the same or different) has the same meaning as the lower alkyl defined above, and the halogen, the cycloalkyl, the aryl and the hererocyclic group have the same meanings as the halogen, the cycloalkyl, the aryl and the hererocyclic group defined above, respectively.

In the examples, of the substituents (A), the substituted lower alkoxy has 1 to 3 independently selected substituents (a). Examples of the substituent (a) are hydroxy, lower alkoxy, lower alkoxy-substituted lower alkoxy, halogen, amino, azido, carboxy and lower alkoxycarbonyl. In the examples of the substituent (a), the lower alkyl moiety of the lower alkoxy and the lower alkoxycarbonyl has the same meaning as the lower alkyl defined above; and the two lower alkyl moieties of the lower alkoxy-substituted lower alkoxy may be the same or different and each has the same meaning as the lower alkyl defined above, and the halogen has the same meaning as the halogen defined above. In the examples of the substituents (A), the substituted aryl and the substituted heterocyalic group each have 1 to 3 independently selected substituents (B) mentioned below.

The substituted aryl, the substituted naphthyl, the substituted phenyl, the substituted heterocyclic ring, the substituted heteroaryl, the substituted cycloalkyl, the substituted cycloalkenyl, the substituted carbon ring formed by combining A and the adjacent two carbon atoms, the substituted heterocyclic ring formed by combining A and the adjacent two carbon atoms, and the substituted carbon ring formed together with the adjacent carbon atom each have 1 to 4 independently selected substituents (B). Examples of the substituents (B) are hydroxy, nitro, amino, carboxy, sulfo, trifluoromethyl, halogen, lower alkyl, lower alkenyl, lower alkynyl, substituted or unsubstituted lower alkoxy, lower alkylamino, di(lower alkyl)amino, substituted or unsubstituted aryl, aryloxy, aralkyl, aralkyloxy, lower alkanoyl, lower alkanoyloxy, aroyl, aroyloxy, aryl-substuituted alkanoyloxy, lower alkoxycarbonyl, lower alkylcarbamoyl, di(lower alkyl) carbamoyl, lower alkoxysulfonyl, lower alkylsulfamoyl and di(lower alkyl)sulfamoyl. In the examples of the substituents (B), the lower alkyl and the alkyl moiety of the lower alkoxy, the lower alkylamino, the di(lower alkyl)amino, the lower alkanoyl, the lower alkanoyloxy, the lower alkoxycarbonyl, the lower alkylcarbamoyl, the di(lower alkyl)carbamoyl, the lower alkoxysulfonyl, the lower alkylsulfamoyl and the di(lower alkyl)sulfamoyl have the same meaning as the lower alkyl defined above; the aryl and the aryl moiety of the aryloxy has the same meaning as th aryl defined above; the halogen, the lower alkenyl and the lower alkynyl have the same meanings as the halogen, the lower alkenyl and the lower alkynyl defined above, respectively; and the two lower alkyl moieties of the di(lower alkyl)amino, the di(lower alkyl) carbamoyl and the di(lower alkyl)sulfamoyl may be the same or different. In the examples of the substituents (B), the aralkyl and the aralkyl moiety of the aralkyloxy include those having 7 to 15 carbon atoms, such as benzyl, phenethyl, benzhydryl and naphthylmethyl; the aryl-substuituted alkyl moiety of the aryl-substuituted alkanoyloxy includes benzyl and phenethyl; and the aroyl and the aroyl moiety of the aroyloxy include benzoyl and naphthoyl. In the examples of the substituents (B), the substituted lower alkoxy and the substituted aryl each have 1 to 3 independently substituents selected from the examples of the substituents (a) mentioned above.

The substituted amino and the substituted carbamoyl each have 1 or 2 independently selected substituents (C). Examples of the substituents (C) are substituted or unsubstituted lower alkyl, and substituted or unsubstituted lower alkoxy. In the examples of the substituents (C), the lower alkyl and the alkyl moiety of the lower alkoxy have the same meaning as the lower alkyl defined above. In the examples of the substituents (C), the substituted lower alkyl and the substituted lower alkoxy each have 1 to 3 independently substituents selected from the examples of the substituents (a) mentioned above.

Hereinafter, compounds represented by formulas (I), (I-A), (I-B), (II), (III), (III-A), (IV) to (XII), (XII-A), (XIII) to (XVIII), and (XVIII-A) will be referred to as Compounds (I), (I-A), (I-B), (II), (III), (III-A), (IV) to (XII), (XII-A), (XIII) to (XVIII) and (XVIII-A), respectively.

The pharmaceutically acceptable salts of Compounds (I), (I-A), (I-B), (II), (III), (III-A), (IV) to (XII), (XII-A), (XIII) to (XVIII) and (XVIII-A) include pharmaceutically acceptable acid addition salts, metal salts, ammonium salts, organic amine addition salts and amino acid addition salts.

The pharmaceutically acceptable acid addition salts include inorganic acid addition salts such as hydrochloride, sulfate, nitrate and phosphate, and organic acid addition salts such as acetate, maleate, fumarate and citrate; the pharmaceutically acceptable metal salts include alkali metal salts such as sodium salt and potassium salt, alkaline earth metal salts such as magnesium salt and calcium salt, aluminium salt and zinc salt; the pharmaceutically acceptable ammonium salts include ammonium and tetramethylammonium; the pharmaceutically acceptable organic amine addition salts include addition salts with morpholine or piperidine; and the pharmaceutically acceptable amino acid addition salts include addition salts with lysine, glycine or phenylalanine.

The anxiolytic other than the adenosine $A_{2A}$ receptor antagonist used in the method of the present invention is not limited as long as it has antianxiety activity. Examples of the anxiolytic include tryptamine reuptake inhibitors such as buspirone, sertraline, paroxetine, nefazodone and fluxetine;

GABA receptor agonists such as benzodiazepines (e.g. diazepam, tofisopam, alprazolam and flutopazepam); corticotropin releasing factor antagonists such as pivagabine; and MAO inhibitors such as amisulpride.

Production of Compounds (I), (I-A), (I-B), (II), (III), (III-A), (IV) to (XII), (XII-A), (XIII) to (XVIII) and (XVIII-A), and pharmaceutically acceptable salts thereof can be conducted readily by those of ordinary skill in this art as evidenced by the teachings of the aforementioned U.S. patents, PCT or European patent application publications, or the like.

Pharmaceutical compositions for administration according to the present invention comprise at least one adenosine $A_{2A}$ receptor antagonist as active ingredient(s) optionally combined with pharmaceutically acceptable carrier(s). These compositions can be administered by any means that achieve their intended purposes. Amounts and regimens for the administration of the pharmaceutical compositions can be readily determined by those with ordinary skill in the art in treating patients suffering from anxiety disorders.

The pharmaceutical compositions described herein can be administered by any suitable method including, without limitation, orally; intranasally; intrapulmonarily; parenterally, such as subcutaneously, intravenously, intramuscularly, intraperitoneally; intraduodenally; transdermally; or buccally.

The dosage administered is an effective amount and depends upon the age, health and weight of the patient, type of previous or concurrent treatment, if any, frequency of treatment, and the nature of the effect desired. Several factors are typically taken into account when determining an appropriate dosage. These factors include age, sex and weight of the patient, the condition being treated, the severity of the condition and the form of the drug being administered.

An "effective amount" is the amount sufficient to affect a beneficial or desired clinical result. An effective amount can be administered in one or more doses.

The adenosine $A_{2A}$ receptor antagonists may preferably be administered in an amount of from about 0.001 to about 20.0 mg per kilogram of body weight. A dosage range of from about 0.01 to about 10 mg per kilogram of body weight is more preferable. Since the adenosine $A_{2A}$ receptor antagonists used in the present invention will eventually be cleared from the bloodstream, re-administration of the pharmaceutical compositions is indicated and preferred.

The adenosine $A_{2A}$ receptor antagonists used in the present invention can also be administered in the form of an implant when compounded with a biodegradable slow-release carrier. Alternatively, the active ingredients can be formulated as a transdermal patch for continuous release of the active ingredient(s) Methods of making implants and patches are well known in the art [Remington's Pharmaceutical Sciences 18th Edition (1990), E. W. Martin ed., Mack Publishing Co., Pa; and Kydonieus ed. (1992). Treatise on controlled drug delivery Marcel Dekker, NY].

In terms of treatment, an effective amount is the amount that is sufficient to palliate, ameliorate, stabilize, reverse or slow the progression of the disease or disorder, or otherwise reduce the pathological consequences of the disease or disorder. The effective amount is generally determined by the physician on a case-by-case basis and is within the skill of one in the art.

In addition to the active ingredient(s), the pharmaceutical compositions according to the present invention can also contain a suitable pharmaceutically acceptable carrier such as an excipient that facilitates processing of the active ingredient(s) into a pharmaceutically acceptable preparation. Preferably, the preparations, particularly those preparations which can be administered orally and which can be used for the preferred type of administration, such as tablets, troches or capsules, and also preparations which can be administered rectally, such as suppositories, as well as suitable solutions for administration by injection or oral administration, contain from about 0.1 to 99 percent, preferably from about 20 to 85 percent of active ingredient(s), together with the excipient. Liquid preparations can, for example, be prepared by dissolving or dispersing the active ingredient(s) in a liquid excipient, such as water, saline, aqueous dextrose, glycerol, or ethanol. The pharmaceutical compositions can also contain other medicinal agent(s), pharmaceutical agent(s), carrier(s), or auxiliary substance(s) such as wetting or emulsifying agent(s), or pH buffering agent(s).

Pharmaceutical compositions according to the present invention are administered by a mode appropriate for the form of composition. Typical routes include subcutaneous, intramuscular, intraperitoneal, intradermal, oral, intranasal, and intrapulmonary (i.e., by aerosol). Pharmaceutical compositions according to the present invention for human use are typically administered orally.

Pharmaceutical compositions for oral, intranasal, or topical administration can be supplied in solid, semi-solid or liquid forms, including tablets, capsules, powders, liquids, and suspensions. Pharmaceutical compositions for injection can be supplied as liquid solutions or suspensions, as emulsions, or as solid forms suitable for dissolution or suspension in liquid prior to injection. For administration via the respiratory tract, a preferred pharmaceutical composition is one that provides a solid, powder, or liquid aerosol when used with an appropriate aerosolizer device. Although not required, pharmaceutical compositions are preferably supplied in unit dosage form suitable for administration of a precise amount. Also contemplated by the present invention are slow release or sustained release forms, whereby relatively consistent levels of the active ingredient(s) are provided over an extended period.

The adenosine $A_{2A}$ receptor antagonists can be administered in a manner compatible with the dosage formulation and in such an amount as will be therapeutically effective. Systemic dosages depend on the age, weight and conditions of the patient and on the administration route.

The pharmaceutical compositions useful in the methods according to the present invention are manufactured in a known manner. The preparation of the pharmaceutical compositions is conducted in accordance with generally accepted procedures for the preparation of pharmaceutical preparations [e.g., Remington's Pharmaceutical Sciences 18th Edition (1990), E. W. Martin ed., Mack Publishing Co., Pa]. Depending on the intended use and mode of administration, it may be desirable to process the active ingredient further in the preparation of the pharmaceutical compositions. Appropriate processing may include sterilizing, mixing with appropriate non-toxic and non-interfering components, dividing into dose units, and enclosing in a delivery device.

The pharmaceutical preparations for oral use can be obtained by combining the active ingredient(s) with solid excipient(s), optionally grinding the resulting mixture, and processing the mixture of granules, after adding suitable auxiliarie(s), if desired or necessary, to obtain tablets.

Suitable excipients include fillers such as saccharides, for example, lactose, sucrose, mannitol or sorbitol; cellulose derivatives; zinc compounds; and/or calcium phosphates such as tricalcium phosphate or calcium hydrogen phosphate; binders such as starch paste, using, for example, maize starch, wheat starch, rice starch or potato starch; gelatin; tragacanth; and/or polyvinylpyrrolidone.

Auxiliaries include flow-regulating agents and lubricants, such as silica, talc, stearic acid or salts thereof, and/or polyethylene glycol. Tablets, caplets or capsule cores are provided with suitable coatings which, if desired, are resistant to gastric juices. For this purpose, concentrated saccharide solutions can be used, which can optionally contain gum Arabic, talc, polyvinyl pyrrolidone, polyethylene glycol and/or titanium dioxide, lacquer solutions, or suitable organic solvents or solvent mixtures. In order to produce coatings resistant to gastric juices, i.e., enteric coatings, solutions of suitable cellulose preparations such as acetylcellulose phthalate or hydroxypropyl methyl cellulose phthalate are used. Dyes or pigments can be added to the tablets or coatings, for example, for identification or in order to characterize combinations of active ingredient doses.

Other pharmaceutical compositions, which can be used orally, include push-fit capsules made of gelatin, as well as soft, sealed capsules made of gelatin and a plasticizer such as glycerol or sorbitol. The push-fit capsules can contain the active ingredient(s) in the form of granules, which can be mixed with filler(s) such as lactose, binders such as starches, and/or lubricant(s) such as talc or magnesium stearate and, optionally, stabilizer(s). In soft capsules, the active ingredient(s) are preferably dissolved or suspended in a suitable liquid, such as fatty oils or liquid paraffin. In addition, stabilizer(s) may be added.

When the adenosine $A_{2A}$ receptor antagonist is used in combination with an anxiolytic other than the adenosine $A_{2A}$ receptor antagonist in the method of treating an anxiety disorder, comprising administering an effective amount of at least one adenosine $A_{2A}$ receptor antagonist in combination with an anxiolytic other than the adenosine $A_{2A}$ receptor antagonist of the present invention, the adenosine $A_{2A}$ receptor antagonist and the anxiolytic other than the adenosine $A_{2A}$ receptor antagonist can be administered to a patient in need thereof either as a single preparation or as a combination of plural preparations, as long as both active ingredients are formulated into a preparation, and a combination of more than two preparations is preferable. Further, when the adenosine $A_{2A}$ receptor antagonist and the anxiolytic other than the adenosine $A_{2A}$ receptor antagonist are used or administered as a combination of plural preparations, these preparations can be used or administered simultaneously or separately at a different time.

When the adenosine $A_{2A}$ receptor antagonist and the anxiolytic other than the adenosine $A_{2A}$ receptor antagonist are administered as a combination of plural preparations, for example, the first component (a) comprising the adenosine $A_{2A}$ receptor antagonist and the second component (b) comprising the anxiolytic other than the adenosine $A_{2A}$ receptor antagonist can be independently formulated into a preparation to make a kit for the treatment, and administered using the kit to the same object via the same route or via different routes, simultaneously or separately at a different time.

Examples of the kit include those which comprise the content and more than two containers (ex. a vial or a bag) which are not limited in material, shape or the like as long as they do not cause denaturation of the ingredients, which are the content, due to the temperature outside or light on storage, elution of the chemical ingredients from the container, and the like, and that are in a form to enable the above first component and the second component which are the content to be administered via different routes (ex. a tube or the like) or via the same route. More specifically, examples of the kit include the kit of the tablets, injection, or the like.

The following non-limiting Test Examples further illustrate the present invention. All references cited herein are hereby incorporated by reference.

Test Example 1

Hole-Board Test in the Mouse

The method followed that described in Arch. Int. Pharmacodyn. Ther., 147, 372-387 (1964) with a slight modification.

Mice were individually placed on a square board (35×35 cm) raised 60 cm above the floor, containing 16 equally spaced holes (25 mm diameter). The number of head-dips occuring during a 5 minute test was counted.

The test compound or vehicle was administered orally 60 minutes before the test.

Results:

Table 1-A shows the effect of Compound A in the Hole-Board Test in the mouse.

Compound A significantly increased the number of head-dips (+63%) and the quadrants entered (+92%) at 3 mg/kg.

Data were analyzed by comparing the result of a tested group with that of a vehicle control group using an unpaired Student's t-test.

TABLE 1-A

| TREATMENT (mg/kg) p.o. −60 min | NUMBER OF HEAD-DIPS | | | NUMBER OF ENTRIES INTO THE 4 QUADRANTS | | |
|---|---|---|---|---|---|---|
| | mean ± s.e.m. | p value | % change from control | mean ± s.e.m. | p value | % change from control |
| Vehicle | 28.6 ± 2.4 | — | — | 12.7 ± 0.8 | — | — |
| Compound A (3) | 46.7 ± 3.2*** | 0.000 | +63% | 24.4 ± 1.7*** | 0.000 | +92% |

***p < 0.001

Table 1-B shows the effect of Compound B in the Hole-Board Test in the mouse Compound B significantly increased the number of head-dips (+45%) at 3 mg/kg.

Data were analyzed by comparing the result of a tested group with that of a vehicle control group using an unpaired Student's t-test.

TABLE 1-B

| TREATMENT (mg/kg) p.o. −60 min | NUMBER OF HEAD-DIPS | | |
|---|---|---|---|
| | mean ± s.e.m. | p value | % change from control |
| Vehicle | 30.2 ± 3.9 | — | — |
| Compound B (3) | 43.9 ± 4.2* | 0.0315 | +45% |

TABLE 1-B-continued

NUMBER OF HEAD-DIPS

| TREATMENT (mg/kg) p.o. −60 min | mean ± s.e.m. | p value | % change from control |
|---|---|---|---|

*p < 0.05

Table 1-C, shows the effect of compound C in the Hole-Board Test in the mouse.

Compound C significantly increased the number of head-dips (+55%) at 10 mg/kg.

Data were analyzed by comparing the result of a tested group with that of a vehicle control group using an unpaired Student's t-test.

TABLE 1-C

NUMBER OF HEAD-DIPS

| TREATMENT (mg/kg) p.o. −60 min | mean ± s.e.m. | p value | % change from control |
|---|---|---|---|
| Vehicle | 30.2 ± 3.9 | — | — |
| Compound C (10) | 46.9 ± 3.4** | 0.0074 | +55% |

**p < 0.01

Test Example 2

Marble Burying Test in the Mouse

The method followed that described in Eur. J. Pharmacol., 126, 223-229 (1986) with a slight modification.

Mice exposed to a novel object (marbles) tend to bury them in the sawdust floor covering.

Mice were individually placed in transparent plastic cages with 25 colored marbles (diameter 1.5 cm) on 5 cm of the sawdust floor. The cage was covered with a similar cage upturned.

The number of marbles covered by sawdust (50% or more) was counted at the end of a 30 minute test.

The test compound or vehicle was administered orally 60 minutes before the test.

Results:

Table 2-A shows the effect of Compound A in the Marble Burying Test in the mouse.

Compound A significantly decreased the number of marbles buried at 3 mg/kg (−50%).

Data were analyzed by comparing the result of treated groups with that of a vehicle control group using an unpaired Student's t-test.

TABLE 2-A

NUMBER OF MARBLES COVERED BY SAWDUST

| TREATMENT (mg/kg) p.o. −60 min | mean ± s.e.m. | p value | % change from control |
|---|---|---|---|
| Vehicle | 20.9 ± 1.4 | — | — |
| Compound A (3) | 10.5 ± 2.9** | 0.004 | −50% |

**p < 0.01

Table 2-B shows the effect of Compound B in the Marble Burying Test in the mouse.

Compound B significantly decreased the number of marbles covered by sawdust (−55%) at 3 mg/kg.

Data were analyzed by comparing the result of treated groups with that of a vehicle control group using an unpaired Student's t-test.

TABLE 2-B

NUMBER OF MARBLES COVERED BY SAWDUST

| TREATMENT (mg/kg) p.o. −60 min | mean ± s.e.m. | p value | % change from control |
|---|---|---|---|
| Vehicle | 20.6 ± 1.1 | — | — |
| Compound B (3) | 9.3 ± 1.9*** | 0.0001 | −55% |

***p < 0.001

Table 2-C shows the effect of Compound C in the Marble Burying Test in the mouse.

Compound C decreased the number of marbles covered by sawdust (−17%) at 10 mg/kg.

Data were analyzed by comparing the result of treated groups with that of a vehicle control group using an unpaired Student's t-test.

TABLE 2-C

NUMBER OF MARBLES COVERED BY SAWDUST

| TREATMENT (mg/kg) p.o. −60 min | mean ± s.e.m. | p value | % change from control |
|---|---|---|---|
| Vehicle | 20.9 ± 1.1 | — | — |
| Compound C (10) | 17.0 ± 1.6 | 0.08 | −17% |

Test Example 3

Learned Helplessness in the Rat

The method followed that described in J. Exp. Psychol., 74, 1-9 (1967) with a slight modification.

Preconditioning with inescapable electric foot shock was given individually to each rat in the shuttle box on day 1. A constant current (1.3 mA) shock generator delivered scrambled, inescapable shocks to the grid floor during 50 minute preconditioning period. Control rats were also individually placed in the identical chamber for 50 minutes, but shock was not given. Conditioned avoidance training session (FR1: buzzer 10 seconds, 0.6 mA foot shock; 5 seconds, interval time; 10 seconds/trial, 15 escape trials) and test session (FR2: 0.6 mA foot shock; 10 seconds, interval time; 0.5 seconds, 0.6 mA foot shock; 10 seconds, interval time; 15 seconds/trial, 15 trials) were performed on day 2 consecutively. FR1 session consisted of 15 trials during which a single shuttle response terminated shock and rats learned how to escape shocks. Subsequent FR2 session consisted of 15 trials during which each rat had to cross from one side of the shuttle box to the other and then crossed back to terminate shock. Shock (0.6 mA) terminated automatically on a trial when the appropriate response requirement was not met within 20 seconds of shock onset.

The test compound or vehicle was administered orally 60 minutes before the test.

The ratio of escape response was calculated from the following formula.

Ratio of escape response(%)=Number of succeeded escape response/15×100

The ratio of intertrial response is calculated from the following formula.

Ratio of intertrial response(%)=Number of crossing the shuttle during intertrial period/15×100

Results:

FIG. 1 shows the effect of compound A in the Learned Helplessness Teat in the rat.

Data were analyzed by comparing the result of a tested group with that of a vehicle control group using a Steel test.

Compound A dose-dependently reversed the escape failure at 1.25 mg/kg and more with a single treatment but did not increase intertrial crossings.

Test Example 4

Elevated Plus-Maze Test in the Rat

The method followed that described in Naunyn. Schmied. Arch. Pharmacol., 327, 1-5 (1984) with a slight modification.

The maze consisted of 4 arms of equal length and width (50×10 cm) arranged in the form of a plus sign (+). Two opposite arms were enclosed by 40 cm high walls (closed arms). The 2 other arms had no walls (open arms). The maze was raised 50 cm above the floor. A rat was placed in the center of the plus-maze and left to explore for 5 minutes. The number of entries into the open and closed arms and the time spent in the open arms was recorded.

The test compound or vehicle was administered orally 60 minutes before the test, respectively.

Results:

Table 3-A shows the effect of Compound A in the Elevated Plus-Maze Test in the rat.

Compound A significantly increased the number of open arm entries (+184%) and the time spent in open arms (+268%) at 3 mg/kg.

Data were analyzed by comparing the result of a treated group with that of a vehicle control group using an unpaired Student's t-test.

TABLE 3-A

| | OPEN ARMS | | | | | |
|---|---|---|---|---|---|---|
| TREATMENT (mg/kg) po −60 min | NUMBER OF ENTRIES | | | TIME SPENT (sec) | | |
| | mean ± s.e.m. | p value | % change from control | mean ± s.e.m. | p value | % change from control |
| Vehicle | 1.9 ± 0.3 | — | — | 38.9 ± 7.7 | — | — |
| Compound A (3) | 5.4 ± 0.7*** | <0.001 | +184% | 143 ± 20.9*** | <0.001 | +268% |

***p < 0.001

Table 3-B shows the effect of Compound B in the Elevated Plus-Maze Test in the rat.

Compound B significantly increased the number of open arm entries (+222%) and the time spent in open arms (+505%) at 1 mg/kg.

Data were analyzed by comparing the result of a treated group with that of a vehicle control group using an unpaired Student's t-test.

TABLE 3-B

| | OPEN ARMS | | | | | |
|---|---|---|---|---|---|---|
| TREATMENT (mg/kg) po −60 min | NUMBER OF ENTRIES | | | TIME SPENT (sec) | | |
| | mean ± s.e.m. | p value | % change from control | mean ± s.e.m. | p value | % change from control |
| Vehicle | 1.8 ± 0.8 | — | — | 15.6 ± 8.1 | — | — |
| Compound B (1) | 5.8 ± 0.8** | 0.0042 | +222% | 94.4 ± 15.2*** | <0.001 | +505% |

**p < 0.01,
***p < 0.001

Table 3-C shows the effect of Compound C in the Elevated Plus-Maze Test in the rat.

Compound-C increased the number of open arm entries (+83%) and the time spent in open arms (+109%) at 30 mg/kg.

Data were analyzed by comparing the result of a treated group with that of a vehicle control group using an unpaired Student's t-test.

TABLE 3-C

| TREATMENT (mg/kg) po −60 min | OPEN ARMS | | | | | |
|---|---|---|---|---|---|---|
| | NUMBER OF ENTRIES | | | TIME SPENT (sec) | | |
| | mean ± s.e.m. | p value | % change from control | mean ± s.e.m. | p value | % change from control |
| Vehicle | 2.3 ± 0.5 | — | — | 26.4 ± 6.6 | — | — |
| Compound C (30) | 4.2 ± 0.8 | 0.0503 | +83% | 55.2 ± 10.7* | 0.0245 | +109% |

*p < 0.05

Test Example 5

Social Interaction Test in the Rat

The method followed that described in Br. J. Pharmacol., 62, 19-24 (1978) with a slight modification.

A pair of male rats were placed in opposite corners of an open-topped arena (50×50×50 cm) and allowed to interact with each other. The time spent in active social interaction (i.e. sniffing, following, grooming, mounting, crawling under or over the partner) was recorded for a 10 minute session.

The test compound or vehicle was administered orally 60 minutes before the test, with each rat of the same pair receiving the same treatment.

Results:

Table 4-A shows the effect of Compound A in the Social Interaction Test in the rat.

Compound A significantly increased the time spent in active social interaction by 57% at 3 mg/kg.

Data were analyzed by comparing the result of a treated group with that of a vehicle control group using an unpaired Student's t-tests.

TABLE 4-A

| TREATMENT (mg/kg) po −60 min | TIME SPENT IN ACTIVE SOCIAL INTERACTION (sec) | | |
|---|---|---|---|
| | mean ± s.e.m. | p value | % change from control |
| Vehicle | 97.5 ± 8.7 | — | — |
| Compound A (3) | 153 ± 11.2** | 0.001 | +57% |

**p < 0.01

Table 4-B shows the effect of Compound B in the Social Interaction Test in the rat.

Compound B significantly increased the time spent in active social interaction by 58% at 3 mg/kg.

Data were analyzed by comparing the result of a treated group with that of a vehicle control group using an unpaired Student's t-tests.

TABLE 4-B

| TREATMENT (mg/kg) po −60 min | TIME SPENT IN ACTIVE SOCIAL INTERACTION (sec) | | |
|---|---|---|---|
| | mean ± s.e.m. | p value | % change from control |
| Vehicle | 89.0 ± 5.7 | — | — |
| Compound B (3) | 141 ± 6.8*** | 0.0001 | +58% |

***p < 0.001

Table 4-C shows the effect of Compound C in the Social Interaction Test in the rat.

Compound C significantly increased the time spent in active social interaction by 35% at 30 mg/kg.

Data were analyzed by comparing the result of a treated group with that of a vehicle control group using an unpaired Student's t-tests.

TABLE 4-C

| TREATMENT (mg/kg) po −60 min | TIME SPENT IN ACTIVE SOCIAL INTERACTION (sec) | | |
|---|---|---|---|
| | mean ± s.e.m. | p value | % change from control |
| Vehicle | 96.2 ± 8.2 | — | — |
| Compound C (30) | 130 ± 9.7** | 0.0016 | +35% |

**p < 0.01

Test Example 6

Hole-Board Test in the Mouse

The method follows that described in Arch. Int. Pharmacodyn. Ther., 147, 372-387 (1964) with a slight modification.

Mice are individually placed on a square board (35×35 cm) raised 60 cm above the floor, containing 16 equally spaced holes (25 mm diameter). The number of head-dips occuring during a 5 minute test is counted.

The test compound or vehicle is administered orally 60 minutes before the test or intraperitoneally 30 minutes before the test, either alone or in combination with other agents. The following other agents are used; benzodiazepines, SSRIs, 5-HT$_1$ receptor agonists, or other anxiolytic agents.

Data are analyzed by comparing the effects of the test compound with those of the combination.

Test Example 7

Marble Burying Test in the Mouse

The method followed that described in Eur. J. Pharmacol., 126, 223-229 (1986) with a slight modification.

Mice exposed to a novel object (marbles) tend to bury them in the sawdust floor covering.

Mice were individually placed in transparent plastic cages with 25 colored marbles (diameter 1.5 cm) on 5 cm of the sawdust floor. The cage was covered with a similar cage upturned.

The number of marbles covered by sawdust (50% or more) was counted at the end of a 30 minute test.

The test compound or vehicle was administered orally 60 minutes before the test either alone or in combination with buspirone or fluoxetine.

Results:

Table 5 shows the effect of the adjunctive treatment of Compound A with buspirone or fluoxetine in the Marble Burying Test in the mouse.

Single adminisitration of Compound A (1 mg/kg), buspirone (15 mg/kg) or fluoxetine (20 mg/kg) showed no significant effects. However, co-administration of Compound A with either buspirone or fluoxetine significantly decreased the number of marbles covered by sawdust by 43% or 52%, respectively.

Data were analyzed by comparing the result of a treated group with that of a vehicle control group using an unpaired Student's t-test.

TABLE 5

| TREATMENT (mg/kg) po −60 min | NUMBER OF MARBLES COVERED BY SAWDUST | | |
|---|---|---|---|
| | mean ± s.e.m. | p value | % change from control |
| Vehicle | 17.1 ± 1.6 | — | — |
| Compound A (1) | 14.1 ± 1.6 | 0.219 | −18% |
| buspirone (15) | 12.7 ± 1.8 | 0.084 | −26% |
| Compound A (1) + buspirone (15) | 9.8 ± 2.1* | 0.010 | −43% |
| fluoxetine (20) | 13.6 ± 2.5 | 0.230 | −20% |
| Compound A (1) + fluoxetine (20) | 8.2 ± 2.4* | 0.010 | −52% |

*p < 0.05

Test Example 8

Elevated Plus-Maze Test in the Rat

The method followed that described in Naunyn. Schmied. Arch. Pharmacol., 327, 1-5 (1984) with a slight modification.

The maze consisted of 4 arms of equal length and width (50×10 cm) arranged in the form of a plus sign (+). Two opposite arms were enclosed by 40 cm high walls (closed arms). The 2 other arms had no walls (open arms). The maze was raised 50 cm above the floor. A rat was placed in the center of the plus-maze and left to explore for 5 minutes. The number of entries into the open and closed arms and the time spent in the open arms was recorded.

The test compound or vehicle was administered orally 60 minutes before the test either alone or in combination with alprazolam.

Results:

Table 6 shows the effect of the adjunctive treatment of Compound A with alprazolam in the Elevated Plus-Maze Test in the rat.

Either Compound A or alprazolam alone showed moderate effect at 1 mg/kg, whereas the combination of both compounds resulted in larger effect on the number of open arm entries (+239%) and the time spent in open arms (+139%).

Data were analyzed by comparing the result of a treated group with that of a vehicle control group using an unpaired Student's t-test.

TABLE 6

| | OPEN ARMS | | | | | |
|---|---|---|---|---|---|---|
| | NUMBER OF ENTRIES | | | TIME SPENT (sec) | | |
| TREATMENT (mg/kg) po −60 min | mean ± s.e.m. | p value | % change from control | mean ± s.e.m. | p value | % change from control |
| Vehicle | 2.3 ± 0.6 | — | — | 37.4 ± 9.5 | — | — |
| Compound A (1) | 3.8 ± 0.8 | 0.112 | +65% | 55.2 ± 12.1 | 0.255 | +48% |
| alprazolam (1) | 4.4 ± 0.9* | 0.045 | +91% | 57.3 ± 12.8 | 0.216 | +53% |
| Compound A (1) + alprazolam (1) | 7.8 ± 1.1*** | <0.001 | +239% | 89.2 ± 12.4** | 0.002 | +139% |

*p < 0.05;
**= p < 0.01;
***= p < 0.001

Test Example 9

Expression of the Immediate Early Gene c-fos

Two to three hours after administration of the test compound in rats or mice, whole brains are removed, embedded in the OCT compound, and frozen on dry ice Coronal sections (10 μm) are cut on the cryostat, thaw-mounted onto gelatin-coated slides, and stored at −80° C. until further processing. Sections are then hybridized with the antisense RNA probes specific to the c-fos transcripts. Antisense RNA probes are prepared by T3, T7 or SP6 polymerases using [$^{35}$S]CTP or UTP in standard conditions. The labeled probes are subjected to partial alkaline hydrolysis to reduce the average probe length to approximately 150 nucleotides. Hybridizations are performed as described in Nature, 58, 424-428 (1995). All slides are then processed to the autoradiography to visualize the hybridized signals.

Immunohistochemical methods are carried out to map the cell groups with FOS positive nuclei.

Test Example 10

Vogel Conflict Test in the Rat

The method followed that described in Psychopharmacol., 21, 1-7 (1971) with a slightr modification.

Male Wistar rats (160-200 g) were deprived of water for 48 hours prior to test session consisting of a 5 minutes period. Each rat was then placed in a test box (25×30×25 cm). The rat was allowed to explore the drinking spout to drink water. When the rat drinks a drip of water, the electric shock (0.16 mA, duration of 0.2 seconds) was delivered from the floor grid. The number of shocks taken in the 5 minutes test punished session was measured.

The test compound or a vehicle was administered orally 60 minutes before the test, respectively.

Results:
Table 7 shows the effect of Compounds C and D in the Vogel Conflict Test in the rat.

Compounds C and D significantly increased the number of shocks (Compound C: +118.8%, Compound D: +89.5%) at 1 mg/kg.

Data were analyzed by comparing the result of a tested group with that of a vehicle control group using an unpaired Student's t-test.

TABLE 7

| TREATMENT (mg/kg) po −60 min | NUMBER OF SHOCKS | | |
|---|---|---|---|
| | mean ± s.e.m | p value | % change from control |
| vehicle | 4.8 ± 1.3 | — | — |
| Compound C (1) | 10.5 ± 2.1* | 0.029 | +118.8% |
| vehicle | 5.7 ± 0.8 | — | — |
| Compound D (1) | 10.8 ± 1.6* | 0.021 | +89.5% |

*p < 0.05

Among the above-described tests, hole-board test (Test Examples 1 and 6) is a model of anxiety disorder, especially for GAD [Eur. J. Pharmacol., 350, 21-29 (1998); and Pol. J. Pharmacol., 49, 79-84 (1997)].

Marble burying test (Test Examples 2 and 7) is a model of anxiety disorder, especially for OCD [Jpn. J. Pharmacol., 68, 65-70 (1995)].

Learned helplessness (Test Example 3) is a model of anxiety disorder, especially for PTSD [Green et al. In: Behavioral models in psychopharmacology: theoretical, industrial, and clinical perspectives, Cambridge University Press, p. 21-49 (1991); and Ann. NY Acad. Sci., 821, 332-351 (1997)].

Elevated plus maze test (Test Examples 4 and 8) is a model of anxiety disorder, especially for GAD, panic disorder, agoraphobia and specific phobia [Psychopharmacol., 161, 314-323 (2002); Jpn. J. Psychopharmacol., 15, 125-133 (1995), and Pol. J. Pharmacol., 49, 79-84 (1997)].

Social interaction test (Test Example 5) is a model of anxiety disorder, especially for GAD and social phobia [Physiol. Behav., 71, 551-557 (2000)].

The vogel conflict test (Test Example 10) is a model of anxiety disorder, especially for GAD [Eur. J. Pharmacol., 463, 67-96 (2003)].

BRIEF DESCRIPTION OF THE DRAWINGS

FIG. 1 depicts the effects of Compound A on learned helplessness (LH) in the rat.

Each column represents the mean (±SEM) ratio of escape response (escape-directed behavior; closed bars) and inter-trial response (general moter activity; hatched bars) during FR2 trial.

## means $p<0.01$ vs Normal group, and * and ** means $p<0.05$ and $p<0.01$ vs IES-Cont. group, respectively (n=10).

BEST MODES FOR CARRYING OUT THE INVENTION

Certain embodiments of the present invention are described in the following examples.

Example 1

Tablets

Tablets having the following composition are prepared in a conventional manner.

Compound A (40 g) is mixed with 286.8 g of lactose and 60 g of potato starch, followed by addition of 120 g of a 10% aqueous solution of hydroxypropyl cellulose. The resultant mixture is kneaded, granulated, and then dried by a conventional method. The granules are refined to give granules used to make tablets. After mixing the granules with 1.2 g of magnesium stearate, the mixture is formed into tablets each containing 20 mg of the active ingredient by using a tablet maker (Model RT-15, Kikusui) having pestles of 8 mm diameter.

The prescription is shown in Table 8.

TABLE 8

| Compound A | 20 mg |
|---|---|
| Lactose | 143.4 mg |
| Potato Starch | 30 mg |
| Hydroxypropyl Cellulose | 6 mg |
| Magnesium Stearate | 0.6 mg |
| | 200 mg |

Example 2

Capsules

Capsules having the following composition are prepared in a conventional manner.

Compound A (200 g) is mixed with 995 g of Avicel and 5 g of magnesium stearate. The mixture is put in hard capsules No. 4 each having a capacity of 120 mg by using a capsule filler (Model LZ-64, Zanashi) to give capsules each containing 20 mg of the active ingredient.

The prescription is shown in Table 9.

TABLE 9

| | |
|---|---|
| Compound A | 20 mg |
| Avicel | 99.5 mg |
| Magnesium Stearate | 0.5 mg |
| | 120 mg |

Example 3

Injections

Injections having the following composition are prepared in a conventional manner.

Compound A (1 g) is dissolved in 100 g of purified soybean oil, followed by addition of 12 g of purified egg yolk lecithin and 25 g of glycerin for injection. The resultant mixture is made up to 1,000 ml with distilled water for injection, thoroughly mixed, and emulsified by a conventional method. The resultant dispersion is subjected to aseptic filtration by using 0.2 μm disposable membrane filters, and then aseptically put into glass vials in 2 ml portions to give injections containing 2 mg of the active ingredient per vial.

The prescription is shown in Table 10.

TABLE 10

| | |
|---|---|
| Compound A | 2 mg |
| Purified Soybean Oil | 200 mg |
| Purified Egg Yolk Lecithin | 24 mg |
| Glycerine for Injection | 50 mg |
| Distilled Water for Injection | 1.72 ml |
| | 2.00 ml |

Example 4

Tablets

Tablets having the following composition are prepared in a conventional manner.

Compound A (20 g) and sertraline (20 g) are mixed with 286.8 g of lactose and 60 g of potato starch, followed by addition of 120 g of a 10% aqueous solution of hydroxypropyl cellulose. The resultant mixture is kneaded, granulated, and then dried by a conventional method. The granules are refined to give granules used to make tablets. After mixing the granules with 1.2 g of magnesium stearate, the mixture is formed into tablets each containing 10 mg of Compound A and 10 mg of sertraline by using a tablet maker (Model RT-15, Kikusui) having pestles of 8 mm diameter.

The prescription is shown in Table 11.

TABLE 11

| | |
|---|---|
| Compound A | 10 mg |
| sertraline | 10 mg |
| Lactose | 143.4 mg |
| Potato Starch | 30 mg |
| Hydroxypropyl Cellulose | 6 mg |
| Magnesium Stearate | 0.6 mg |
| | 200 mg |

The invention claimed is:

1. A method of treating generalized anxiety disorder, consisting essentially of administering, to a human in need thereof, an effective amount of (E)-8-(3,4-dimethoxystyryl)-1,3-diethyl-7-methylxanthine or a pharmaceutically acceptable salt thereof as the sole active ingredient.

2. A method of treating generalized anxiety disorder, consisting essentially of orally administering, to a human in need thereof, an effective amount of (E)-8-(3,4-dimethoxystyryl)-1,3-diethyl-7-methylxanthine or a pharmaceutically acceptable salt thereof as the sole active ingredient.

3. A method of treating obsessive-compulsive disorder, consisting essentially of administering, to a human in need thereof, an effective amount of (E)-8-(3,4-dimethoxystyryl)-1-3-diethyl-7-methylxanthine or a pharmaceutically acceptable salt thereof as the sole active ingredient.

4. A method of treating panic disorder, consisting essentially of administering to a human in need thereof, an effective amount of (E)-8-(3,4-dimethoxystyryl)-1,3-diethyl-7-methylxanthine or a pharmaceutically acceptable salt thereof as the sole active ingredient.

5. A method of treating agoraphobia, consisting essentially of administering, to a human in need thereof, an effective amount of (E)-8-(3,4-dimethoxystyryl)-1,3-diethyl-7-methylxanthine or a pharmaceutically acceptable salt thereof as the sole active ingredient.

6. A method of treating social phobia, consisting essentially of administering, to a human in need thereof, an effective amount of (E)-8-(3,4-dimethoxystyryl)-1,3-diethyl-7-methylxanthine or a pharmaceutically acceptable salt thereof as the sole active ingredient.

* * * * *